United States Patent
Castanon et al.

(10) Patent No.: US 10,092,314 B2
(45) Date of Patent: Oct. 9, 2018

(54) SAFETY SCALPEL WITH REPLACEABLE BLADE CARTRIDGE

(71) Applicant: MEDIPURPOSE PTE LTD

(72) Inventors: Scott Castanon, Carlsbad, CA (US); Dylann Ceriani, San Diego, CA (US)

(73) Assignee: MEDIPURPOSE PTE LTD, Singapore (SG)

( * ) Notice: Subject to any disclaimer, the term of this patent is extended or adjusted under 35 U.S.C. 154(b) by 372 days.

(21) Appl. No.: 14/633,284

(22) Filed: Feb. 27, 2015

(65) Prior Publication Data

US 2016/0249947 A1    Sep. 1, 2016

(51) Int. Cl.
*A61B 17/3213* (2006.01)
*A61B 17/3211* (2006.01)

(52) U.S. Cl.
CPC ...... *A61B 17/3211* (2013.01); *A61B 17/3213* (2013.01); *A61B 2017/32113* (2013.01)

(58) Field of Classification Search
CPC ...... A61B 17/3211; A61B 2017/32113; A61B 2017/32116; B26B 5/001
USPC ............................ 30/161, 162; 606/166, 167
See application file for complete search history.

(56) References Cited

U.S. PATENT DOCUMENTS

| | | | |
|---|---|---|---|
| 4,949,458 A * | 8/1990 | Davis | B26B 29/02 30/162 |
| 5,071,426 A * | 12/1991 | Dolgin | A61B 17/3211 30/151 |
| 5,250,063 A * | 10/1993 | Abidin | A61B 17/3213 30/151 |
| 5,403,337 A | 4/1995 | Platts | |
| 5,481,804 A | 1/1996 | Platts | |
| 5,496,340 A * | 3/1996 | Abidin | A61B 17/3213 30/151 |
| 5,569,282 A * | 10/1996 | Werner | A61B 17/3211 30/162 |
| 5,827,309 A * | 10/1998 | Jolly | A61B 17/32 606/167 |
| 5,938,676 A | 8/1999 | Cohn | |
| 6,623,499 B1 | 9/2003 | Andreini | |
| 7,172,611 B2 * | 2/2007 | Harding | A61B 17/3213 606/167 |

(Continued)

FOREIGN PATENT DOCUMENTS

| | | |
|---|---|---|
| GB | 2017559 A | 10/1979 |
| WO | 2004017844 A1 | 3/2004 |
| WO | 2014089369 A1 | 6/2014 |

OTHER PUBLICATIONS

International Search Report and Written Opinion in PCT/SG2010/050390, dated Feb. 11, 2016.

*Primary Examiner* — Jason Daniel Prone
*Assistant Examiner* — Richard Crosby, Jr.
(74) *Attorney, Agent, or Firm* — Troutman Sanders LLP; Ryan A. Schneider; Brennan M. Carmody

(57) ABSTRACT

In an embodiment, there is a safety scalpel having a handle, and a replaceable blade cartridge assembly that is releasably attached to the handle. The handle comprises a first end and a second end. The blade cartridge assembly comprises a housing that can be slideably mounted onto the second end of the handle, a blade holder that can be disposed within the housing, and a blade that can be attached to the blade holder. The safety scalpel has a resilient lock member that prevents the cartridge assembly from being detached from the handle during use.

24 Claims, 26 Drawing Sheets

(56) References Cited

U.S. PATENT DOCUMENTS

| | | | | |
|---|---|---|---|---|
| RE42,507 E * | 6/2011 | Wilkinson | ......... | A61B 17/3213 30/151 |
| 8,015,712 B2 * | 9/2011 | Yi | ...................... | A61B 17/3213 30/162 |
| 8,136,251 B2 * | 3/2012 | Endo | .................. | A61B 17/3211 30/162 |
| 8,156,653 B2 * | 4/2012 | Austria | .............. | A61B 17/3213 30/161 |
| 8,181,352 B1 * | 5/2012 | Shackelford, Sr. | ......................... | A61B 17/3213 30/162 |
| 8,464,430 B2 * | 6/2013 | Cote | .................. | A61B 17/3211 30/162 |
| 8,567,072 B2 * | 10/2013 | Yi | ...................... | A61B 17/3213 30/162 |
| 9,622,773 B2 * | 4/2017 | Austria | .............. | A61B 17/3213 |
| 2004/0158269 A1 | 8/2004 | Holman | | |
| 2006/0100650 A1 * | 5/2006 | Kiehne | .............. | A61B 17/3213 606/167 |
| 2006/0241664 A1 * | 10/2006 | Lam | .................. | A61B 17/3211 606/167 |
| 2009/0192538 A1 * | 7/2009 | Sandel | ............... | A61B 17/3213 606/167 |
| 2011/0106122 A1 | 5/2011 | Cetola | | |
| 2016/0249947 A1 | 9/2016 | Castanon | | |

* cited by examiner

SAFETY SCALPEL WITH REPLACEABLE BLADE CARTRIDGE

TECHNICAL FIELD

Embodiments of the invention relate to surgical cutting instruments and more particularly, to a safety scalpel comprising a blade cartridge releasably attached to a handle.

BACKGROUND

A conventional scalpel used in the healthcare industry includes a metal handle and a disposable blade that is mounted on the handle prior to use, and removed after use. The process of mounting and dismounting of the blade is a difficult and dangerous procedure as it exposes the medical practitioner to potential injury from the exposed blade and contamination due to blood that may be present on the blade. Further, sharps injuries may also occur during an operation as the surgeon passes the exposed scalpel to a colleague.

An example of a safety scalpel with a releasable blade cartridge is described in U.S. Pat. No. 5,938,676 (Cohn). Although Cohn describes a slidable shield which is slidable to cover the blade when the scalpel is to be disposed, a user is required to push the shield in a forward direction to cover the blade. This action is counter intuitive because it differs from a conventional direction of use in conventional box cutter devices. U.S. Pat. No. 8,567,072 (Yi) describes another example of a safety scalpel with a detachable blade cartridge. The safety scalpel in Yi is adapted to extend and retract by pushing downward on the button and then sliding along the shield to change its position.

The blade cartridge with an extended blade may be inadvertently detached and this may cause potential injury from the exposed blade. To avoid the danger of an exposed blade when the blade cartridge is detached for replacement, some prior art safety scalpels include arrangements in which the blade is self-retractable into the handle or the blade cartridge. Such self-retracting safety scalpels are continually biased towards the retracted position and into the handle using a retractable blade holder by having spring mechanisms arranged to bias the blade holder rearward. However, such self-retracting safety scalpels still require the user to initiate an action to retract the blade. If the user forgets to retract the blade and proceed to remove the blade cartridge with the extended blade, potential injury will still be caused during removal of the blade cartridge.

SUMMARY

In an embodiment, there is a safety scalpel comprising:
a handle;
a blade cartridge releasably attached to the handle, the blade cartridge comprising:
a blade;

a housing; and a blade holder in communication with the blade, wherein the blade holder is configured to allow the blade to extend between a stowed position in a pre-cutting state of the blade holder and a cutting position upon activation of the blade holder; and a resilient lock member disposed within the housing, wherein the resilient lock member is in an unbiased condition when the blade holder is in the pre-cutting state, and wherein the resilient lock member is configured to engage the blade holder to lock the blade cartridge to the handle when the blade is in the cutting position upon activation of the blade holder.

The resilient lock member may be arranged to be moved by the blade holder into a locking aperture of the handle to lock the blade cartridge to the handle when the blade is in the cutting position upon activation of the blade holder.

The resilient lock member may be integral with the housing.

The resilient lock member may comprise a resilient arm portion and a catch extending from the resilient arm portion.

The blade holder may include an inclined surface adapted to engage the resilient arm portion of the resilient lock member and allow the catch of the resilient lock member to be moved into the locking aperture to lock the blade cartridge to the handle when the blade is in the cutting position upon activation of the blade holder.

The blade cartridge may comprise a blade lock mechanism having a ramp adapted to abut the blade holder to prevent movement of the blade in the stowed position before the handle is inserted.

The blade cartridge may comprise a blade lock mechanism having a housing ramp provided on the housing, wherein a handle ramp is provided on the handle, wherein the handle ramp is adapted to push on a housing ramp upon insertion of the handle, to move the housing ramp out of an aperture in the blade holder.

The blade holder may include an activation member configured to be pressed down to enable the blade to slide between the stowed position when the blade holder is in a pre-cutting state and the cutting position upon activation of the blade holder.

The activation member may be configured to engage the housing to prevent movement of the blade when the blade holder is in the pre-cutting state.

The safety scalpel may further comprise a flip guard provided above the activation member.

The activation member may include an embedded button.

The safety scalpel may further comprise a slide guard provided below the activation member.

The safety scalpel may further comprise a button guard provided on the housing and around the activation member to prevent inadvertent activation of the blade holder.

The safety scalpel may further comprise a cartridge release mechanism arranged for allowing release of the blade cartridge upon exerting a force perpendicular to a direction of movement of the blade holder along a longitudinal axis of the handle.

The cartridge release mechanism may comprise a resilient lift tab provided on the blade cartridge wherein the lift tab is arranged adjacent a recess on the handle for allowing release of the blade cartridge when the blade is in the stowed position.

The housing may comprise a first housing part and a second housing part ultrasonically welded together to form the housing.

The housing may comprise a cantilever member adapted for releasably mounting the blade cartridge to the handle.

The blade cartridge may comprise snap features located on opposing sides of the housing, wherein the snap features are adapted to releasably attach the blade cartridge to the handle.

The blade cartridge may comprise a snap feature adapted to engage with an aperture in the handle.

The blade cartridge may comprise a portion configured to move in tandem with the snap feature, and the portion is moveable by the blade holder.

In an embodiment, there is a replaceable blade cartridge for releasably attaching to a handle to form a safety scalpel, the replaceable blade cartridge comprising
- a blade;
- a housing;
- a blade holder in communication with the blade, wherein the blade holder is configured to allow the blade to extend between a stowed position in a pre-cutting state of the blade holder and a cutting position upon activation of the blade holder; and
- a resilient lock member disposed within the housing, wherein the resilient lock member is in an unbiased condition when the blade holder is in the pre-cutting state, and wherein the resilient lock member is configured to engage the blade holder to lock the blade cartridge to the handle when the blade is in the cutting position upon activation of the blade holder.

The resilient lock member may be arranged to be moved by the blade holder into a locking aperture of the handle to lock the blade cartridge to the handle when the blade is in the cutting position upon activation of the blade holder.

The resilient lock member may be integral with the housing.

The resilient lock member may comprise a resilient arm portion and a catch extending from the resilient arm portion.

The blade holder may comprise an inclined surface adapted to engage the resilient arm portion of the resilient lock member and allow the catch of the resilient lock member to be moved into the locking aperture to lock the blade cartridge to the handle when the blade is in the cutting position upon activation of the blade holder.

The blade holder may include an integral activation member configured to be pressed down to enable sliding of the blade holder and the blade.

The activation member may be configured to engage the housing to prevent movement of the blade when the blade holder is in the pre-cutting state.

The activation member may include an embedded button.

In an embodiment, there is a method of operating a safety scalpel, the method comprising the steps of:
- sliding a blade of a blade cartridge on a handle in a longitudinal direction, the blade cartridge comprising:
  - the blade;
  - a housing;
  - a blade holder in communication with the blade, wherein the blade holder is configured to allow the blade to extend between a stowed position in a pre-cutting state of the blade holder and a cutting position upon activation of the blade holder; and
  - a resilient lock member disposed within the housing, wherein the resilient lock member is in an unbiased condition when the blade holder is in the pre-cutting state, and wherein the resilient lock member is configured to engage the blade holder to lock the blade cartridge to the handle when the blade is in the cutting position upon activation of the blade holder; and
- sliding the blade forward to the cutting position, and to move the resilient lock member into the locking aperture to lock the blade cartridge onto the handle when the blade is in the cutting position.

The step of sliding the blade holder may include pressing an activation member of the blade holder in a direction perpendicular to a handle motion to disengage the activation member from the housing.

In an embodiment, there is a blade housing adapted to support a blade holder in communication with a surgical blade for linear sliding in a safety scalpel, the blade housing comprising:
- a first housing; and
- a second housing adapted for attaching to the first housing to form a cavity for supporting the blade holder and the surgical blade, wherein the blade housing is adapted to be mounted to a handle of the safety scalpel;
- a resilient lock member disposed within the blade housing, wherein the resilient lock member is in an unbiased condition when the blade is in a stowed position and the blade holder is in a pre-cutting state, and wherein the resilient lock member is configured to engage the blade holder to lock the blade housing to the handle when the blade is in a cutting position upon activation of the blade holder; and
- a blade lock mechanism comprising a resilient ramp, and a lock mechanism adapted for locking the blade to the handle in a stowed position, wherein the ramp is adapted to bias the lock mechanism upon engagement with the handle.

BRIEF DESCRIPTION OF DRAWINGS

Various embodiments of the invention will now be described, by way of example only, and with reference to the accompanying drawings in which.

DESCRIPTION

While exemplary embodiments pertaining to the invention have been described and illustrated, it will be understood by those skilled in the technical field that many variations or modifications involving particular design, implementation or construction are possible and may be made without deviating from the inventive concepts described herein.

Figure 1A:
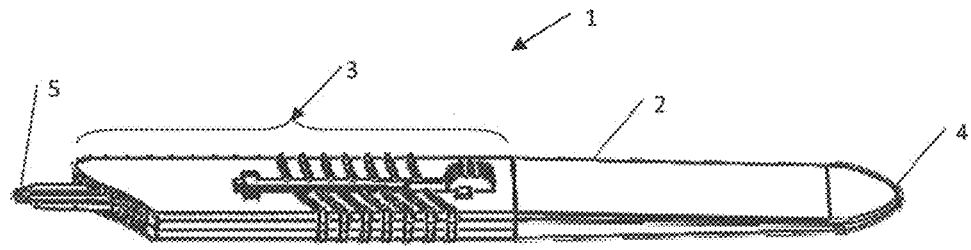
FIG. 1A is a top perspective view of a safety scalpel in a stowed position in a pre-cutting state of a blade holder.
Figure 1B:
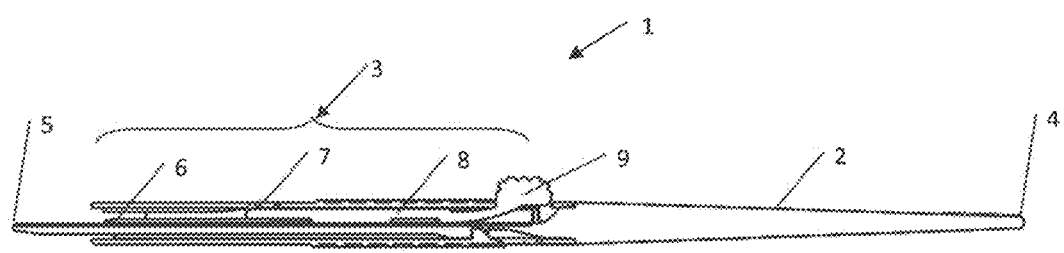
FIG. 1B is a side section view of the safety scalpel.
Figure 1C:
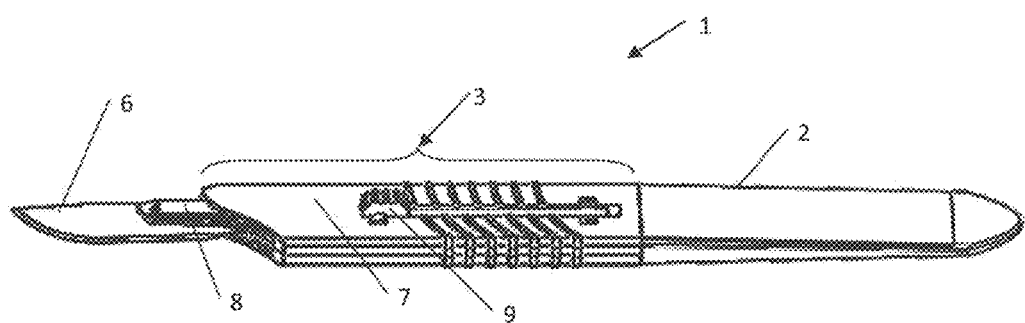
FIG. 1C is a top perspective view of the safety scalpel when a blade is in a cutting position upon activation of a blade holder.

FIG. 1A is a top perspective view of a safety scalpel 1 in a stowed configuration and in a pre-cutting condition in accordance with an embodiment. The safety scalpel 1 comprises a handle 2, and a blade cartridge 3 releasably attached to the handle 3. The handle 2 includes a first end 4 and a second end 5. Referring to FIG. 1B, the blade cartridge 3 includes a blade 6, a housing 7, and a blade holder 8 in communication with the blade 6. The blade holder 8 may be configured to allow the blade 6 to extend between a stowed position in a pre-cutting state of the blade holder 8 and a cutting position upon activation of the blade holder 8. For example as shown in FIGS. 1B and 1C, the blade holder 8 may include an activation member 9 arranged to be slidable along a longitudinal axis of the handle 2.

Figure 2A:
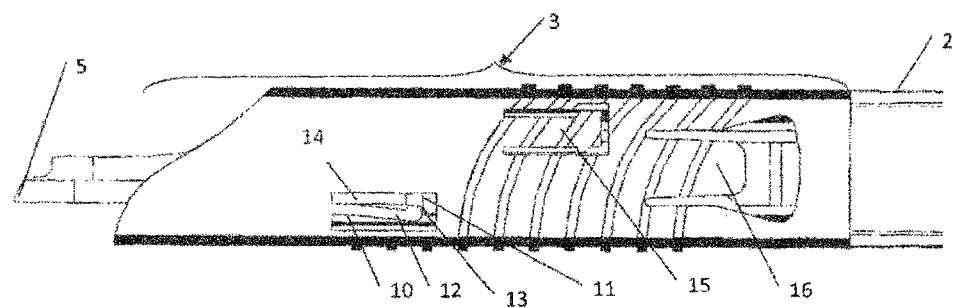
FIG. 2A is a rear view of the safety scalpel in a stowed position in a pre-cutting state of a blade holder.

The safety scalpel 1 also comprises a resilient lock member 10 which will be described in further detail with reference to FIGS. 2A to 2C. Referring to FIG. 2A, the resilient lock member 10 may be disposed within the housing 7 wherein the resilient lock member 10 is in an unbiased condition when the blade holder 8 is in the pre-cutting state, and wherein the resilient lock member 10 does not engage a locking aperture 11 of the handle 2. The resilient lock member 10 may be configured to engage the blade holder 8 to lock the blade cartridge 3 to the handle 2 when the blade 6 is in the cutting position upon activation of the blade holder 8. In an example, the resilient lock member 10 may be arranged to be moved by the blade holder 8 into a locking aperture 11 of the handle 2 to lock the blade cartridge 3 to the handle 2.

Figure 2B:
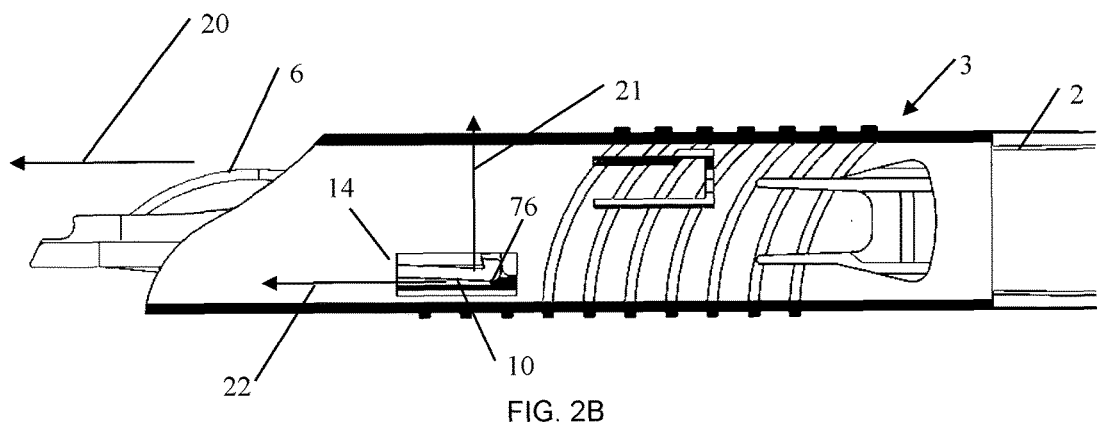
FIG. 2B is a rear view of the safety scalpel between the stowed position in a pre-cutting state of a blade holder and moving towards a cutting position upon activation of the blade holder.

In particular, referring to FIG. 2B in which the safety scalpel 1 is being moved from the stowed configuration towards a cutting configuration upon activation of the blade holder 8 in a direction of travel 20, the resilient lock member 10 may be configured to be moved in a direction 21 by the blade holder 8 into a locking aperture 11 of the handle 2 to lock the blade cartridge 3 to the handle 2 upon activation of the blade holder 8. The direction 21 of movement of the resilient lock member 10 may be substantially perpendicular to a direction 22 of movement of the blade holder 8 and the direction of travel 20 of the blade 6.

Still further, in an example, the resilient lock member 10 may comprise an arm 12 and a catch 13. The arm 12 may be adapted to deflect upon engagement with a ramp 76 of the handle 2 of the safety scalpel 1. The ramp 76 may include a surface adapted to engage a surface of the resilient lock member 10 to bias the resilient lock member 10 in a direction 21 to engage with the locking aperture 11.

In another example, the arm 12 may be a resilient arm portion and the catch 13 extends from the resilient arm portion. The blade holder 8 may also include an inclined surface adapted to engage the resilient arm portion of the resilient lock member 10 and allow the catch of the resilient lock member 10 to be moved into the locking aperture to lock the blade cartridge 3 to the handle 2 when the blade 6 is in the cutting position upon activation of the blade holder 8.

The resilient lock member 10 may be integral with the housing 7 and may extend from an opening 14 of the housing 7. The housing 7 may also comprise a catch 15 and a release tab 16 for attaching to a corresponding slot in the handle 2 to releasably attach the blade cartridge 3 to the handle 2.

Figure 2C:
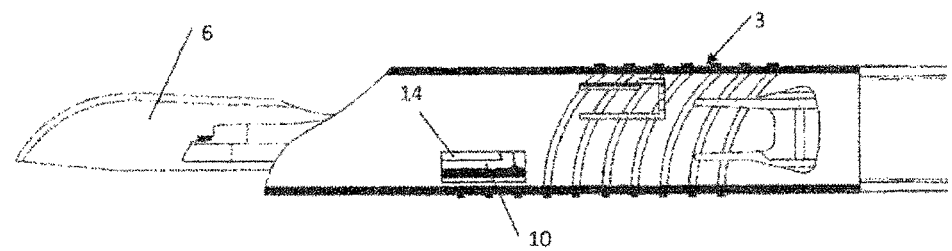
FIG. 2C is a rear view of the safety scalpel when a blade is in the cutting position upon activation of the blade holder.

FIG. 2C is a rear view of the safety scalpel 1 when the blade 6 is in the cutting position upon activation of the blade holder 8. Referring to FIG. 2C, the blade 6 is extended in the cutting position and the blade cartridge 3 is locked to the handle 2 through the resilient lock member 10 in engagement with the locking aperture 11 of the handle 2.

Figure 3:
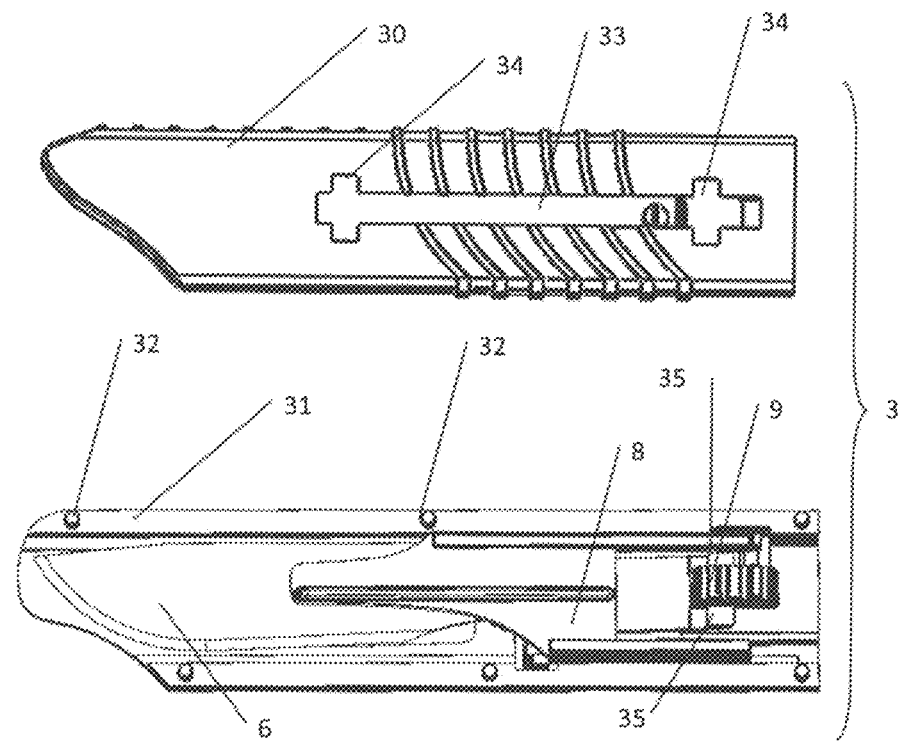
FIG. 3 illustrates components of a blade cartridge.
Figure 4:
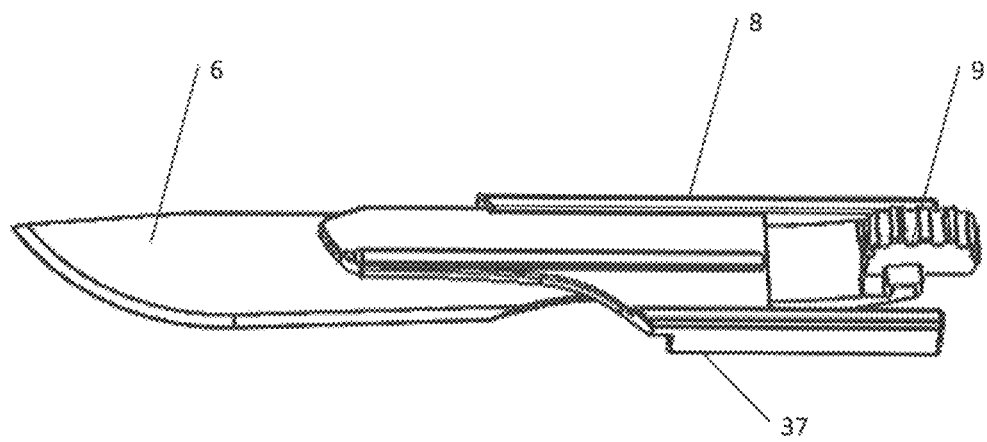
FIG. 4 is a top perspective view of a blade holder with a blade.

FIG. 3 and FIG. 4 illustrate components of the blade cartridge 3. The blade cartridge 3 may include a first housing part 30 and a second housing part 31 which, upon assembly, form the housing 7 for housing the blade 6, and the blade holder 8. For example, the second housing part 31 may include a plurality of joining portions 32 for attaching the first housing part 30 to the second housing part 31 through manufacturing methods for joining plastics such as ultrasonic welding. The housing 7 may be adapted to be mounted to a handle of the safety scalpel 1.

The first housing part 30 has a slot 33 extending longitudinally on a top side of the housing 7 and is adapted for allowing the blade holder 8 to slide between a pre-cutting state when the blade 6 is in a stowed position and a cutting state when the blade 6 is in a cutting position upon activation of the blade holder 8. The slot 33 may include cut-outs 34 shaped to receive the activation member 9 of the blade holder 8. The activation member 9 may include extended portions 35 to be received in the cut-outs 34. In a stowed position of the blade 6, the extended portions 35 of the activation member 9 abut surfaces (not shown in FIG. 3) in the housing 7. The blade housing 7 may also be adapted to support a surgical blade for linear sliding of the blade in the safety scalpel 1.

The blade holder 8 may be configured to be slidably mounted within a cavity of the housing 7. Referring to FIG. 4, the blade holder 8 may be configured to slidably engage the handle 2 and the housing 7. Specifically, the blade holder 8 includes side walls 37 for sliding within the cavity of the housing 7. The activation member 9 may be integral with the blade holder 8.

Figure 5A:
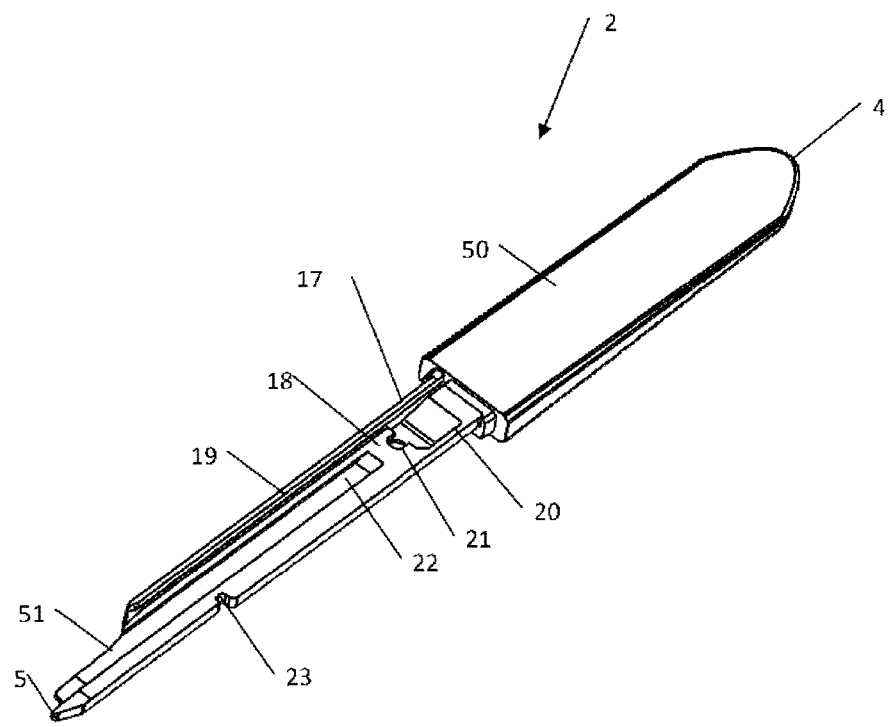
FIG. 5A is a top perspective view of a handle for a safety scalpel.
Figure 5B:
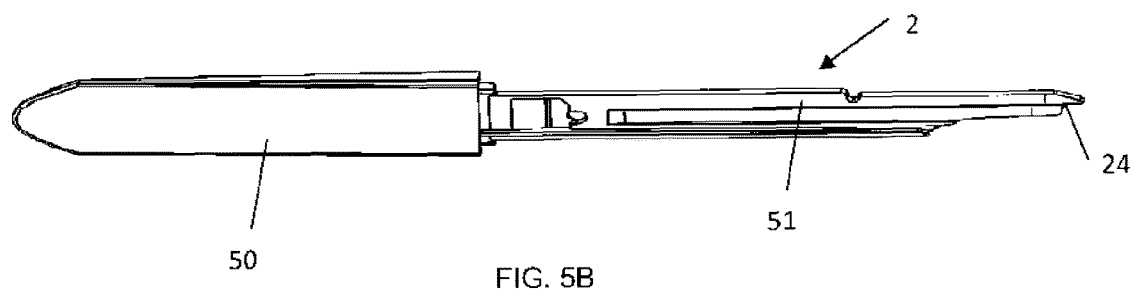
FIG. 5B is a side view of FIG. 5A.

FIG. 5A is a top perspective view of the handle 2 for the safety scalpel 1, and FIG. 5B is a side view of the handle 2. The handle 2 may include a holding portion 50 and a blade cartridge receiving portion 51. The holding portion 50 may extend from the first end 4 to an approximate midpoint. The blade cartridge receiving portion 51 may extend from the approximate midpoint to the second end 5.

The blade cartridge receiving portion 51 of the handle 2 may be adapted to be received in a hollow cavity of the cartridge assembly 3. Further, the blade cartridge receiving portion 51 of the handle 2 may be configured to slidably engage the blade cartridge assembly 3. For example, a longitudinal groove feature 22 may be provided in the blade cartridge receiving portion 51 to enable sliding of a blade holder of the blade cartridge. Still further, the blade cartridge receiving portion 51 may include a side wall 17 extending from a top surface 18 of the blade cartridge receiving portion 51. The side wall 17 may include a side wall surface 19 adapted to slidably engage the housing of the blade cartridge assembly 3.

The blade cartridge receiving portion 51 includes a locking aperture 23 configured to receive a portion of the resilient locking member 8 for locking the blade cartridge assembly 3 to the handle 2 when the safety scalpel 1 is in use, i.e. when the blade 6 is in a cutting position. In the stowed position of the blade 6, the resilient locking member 8 does not engage the locking aperture 23.

The handle 2 may have a blade cartridge lock mechanism for locking the cartridge assembly 3 to the handle 2 in the stowed position of the blade 6. The blade cartridge lock mechanism may comprise a tab receiving aperture 21 configured to receive a tab of the blade cartridge assembly 3. The tab may be a release tab integral with the housing 7 wherein the tab has a protrusion for engaging the tab receiving aperture 21. Further, the blade cartridge lock mechanism may comprise a sloped recess 20 in the blade cartridge receiving portion 51 of the handle 2. The blade cartridge lock mechanism may also be adapted to have a locating surface 21a for guiding the release tab in the cartridge into the tab receiving aperture 21 on the handle 2.

Figure 6A:
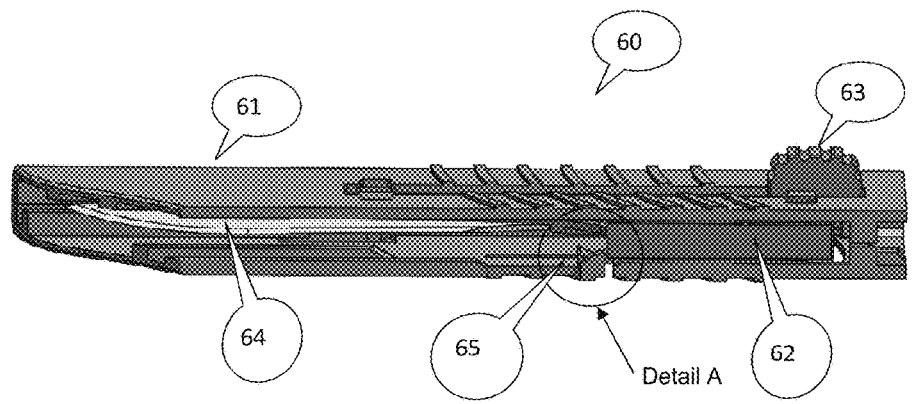
FIG. 6A is a perspective section view of a blade cartridge before assembly to a scalpel handle.

FIG. 6A is a perspective view of a blade cartridge 60 according to an embodiment, before assembly to a scalpel handle. The blade cartridge 60 includes a blade housing 61 that is partially removed for a clearer view of components in the blade cartridge 60. A blade holder 62 is slidably mounted within a cavity of the housing 61, and is adapted to support a surgical blade 64. For example, the blade holder 62 may include surfaces for linear sliding along corresponding guide surfaces of the blade housing 61.

The blade cartridge 60 may comprise a resilient blade lock mechanism 65 formed in the housing 61. The resilient blade lock mechanism 65 may have a ramp adapted to abut the blade holder 62 to prevent movement of the blade 64 in a stowed position before the handle is inserted. The blade holder 62 is in a pre-cutting state when the blade 64 is in the stowed position.

Figure 6B:
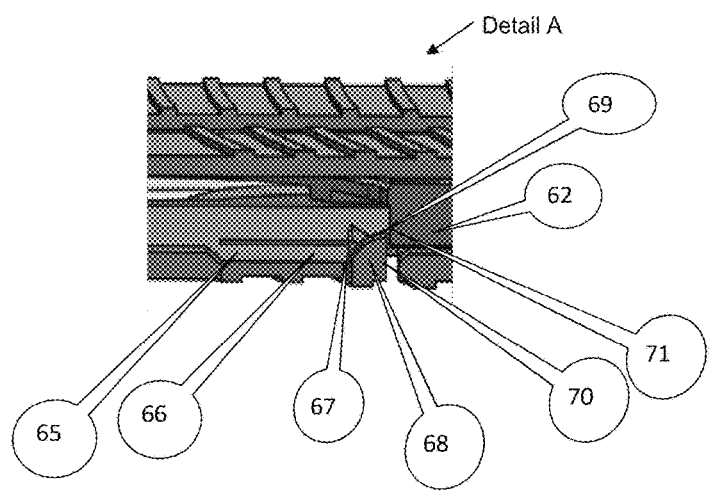
FIG. 6B is a detailed section view of FIG. 6A.

FIG. 6B is a detailed view (Detail A) of an example of a design of the resilient blade lock mechanism 65.

Figure 7A:
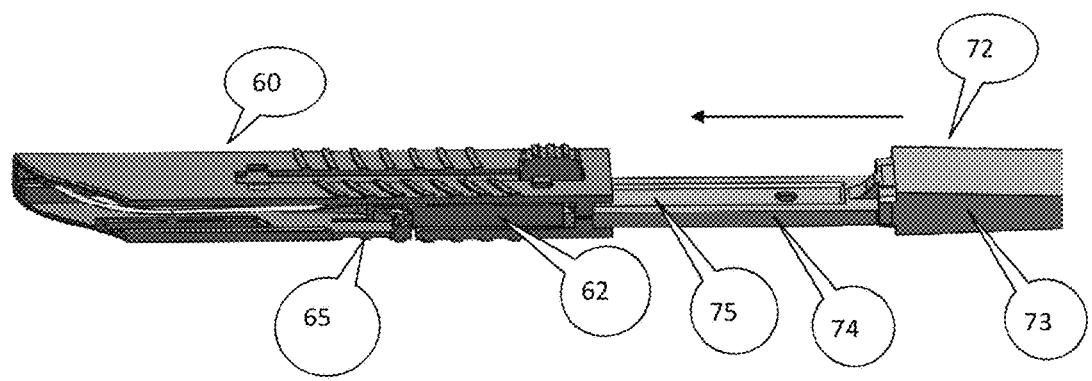
FIG. 7A is a perspective section view of a blade cartridge before assembly to a scalpel handle.
Figure 7B:
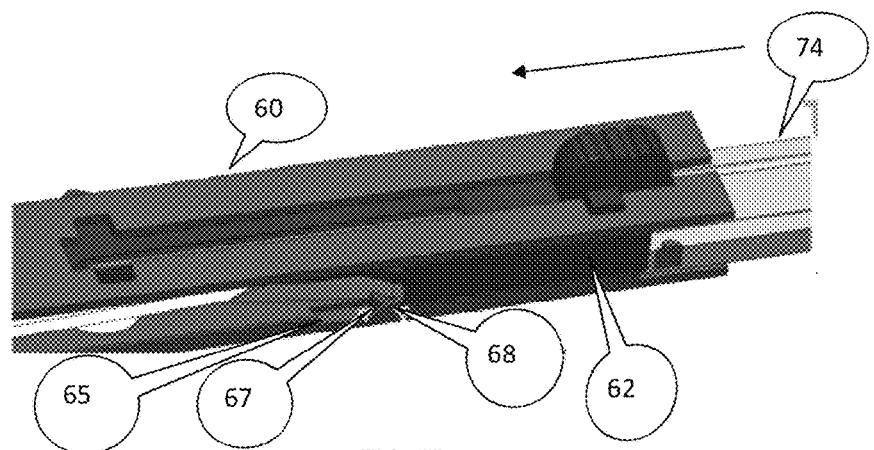
FIG. 7B is a perspective section view of the blade cartridge before assembly to a scalpel handle.
Figure 7C:
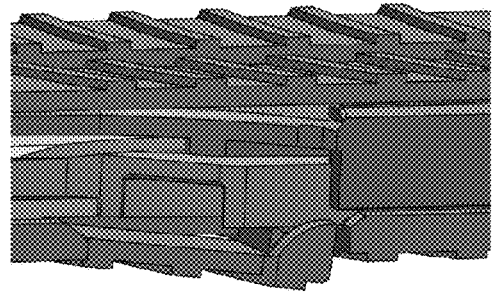
FIG. 7C is a detailed section view of the blade cartridge during assembly to a scalpel handle.
Figure 7D:
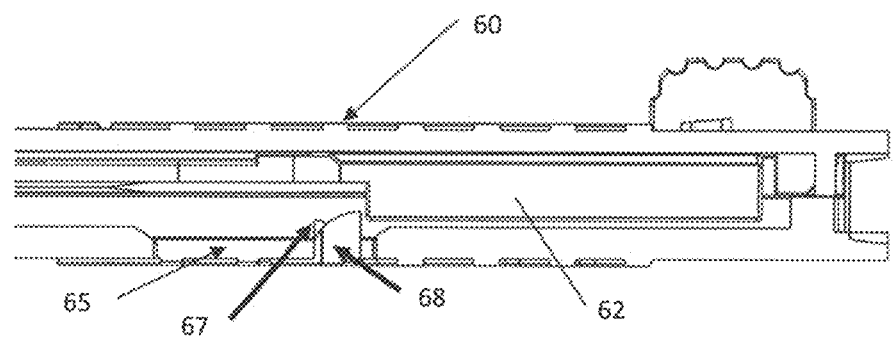
FIG. 7D is a section view of the blade cartridge before assembly to a scalpel handle.
Figure 7E:
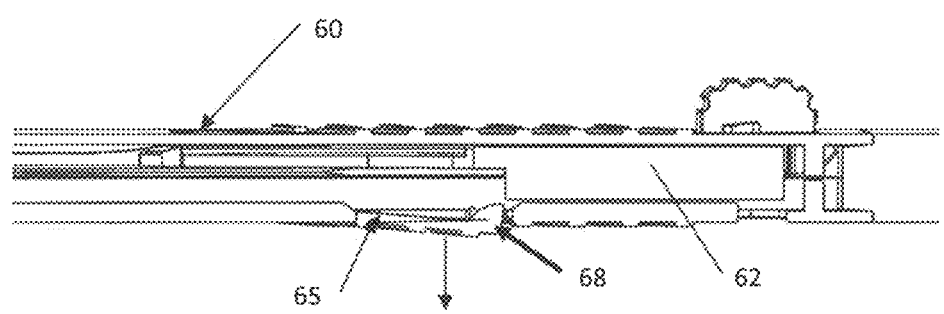
FIG. 7E is a section view of the blade cartridge during assembly to a scalpel handle.

FIG. 7A is a perspective view of the blade cartridge 60 in a process of assembly to a scalpel handle 72 having a handle portion 73 and a blade receiving portion 74. The blade receiving portion 74 may include a groove 75 adapted for slidable movement of the blade holder 62 relative to the handle 72. FIG. 7B is a partial perspective view of the blade cartridge 60 before assembly. FIG. 7D and FIG. 7E are section views of the blade cartridge 60 before and during assembly of the handle.

Referring to the abovementioned figures, the blade lock mechanism 65 comprising a resilient ramp 66, and a lock mechanism 68 for locking the blade 64 so as to prevent movement of the blade holder 62 prior to assembly to a handle. The ramp 66 may be integral with the blade housing 61 and may be adapted to bias the lock mechanism away from the blade holder 62 upon engagement with the scalpel handle 72. For example, the ramp 66 may comprise a sloped surface 69 shaped to lead in the scalpel handle 72. Due to the resilience properties of the ramp 66, the lock mechanism 68 is disengaged from the blade holder 62.

In another example, the blade cartridge 60 may comprise a resilient blade lock mechanism in which the ramp 66 may be configured to engage comprise a handle ramp (not shown) provided on the handle 72. Upon insertion of the handle 72, the handle ramp is adapted to push on the ramp 66 to move the ramp 66 out of an aperture in the blade holder 62.

Figure 8A:
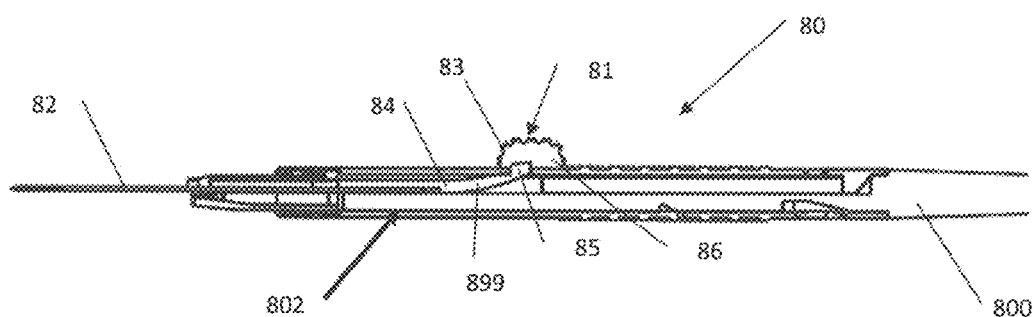
FIG. 8A is a section view of a safety scalpel when a blade is in a cutting position upon activation of a blade holder.
Figure 8B:
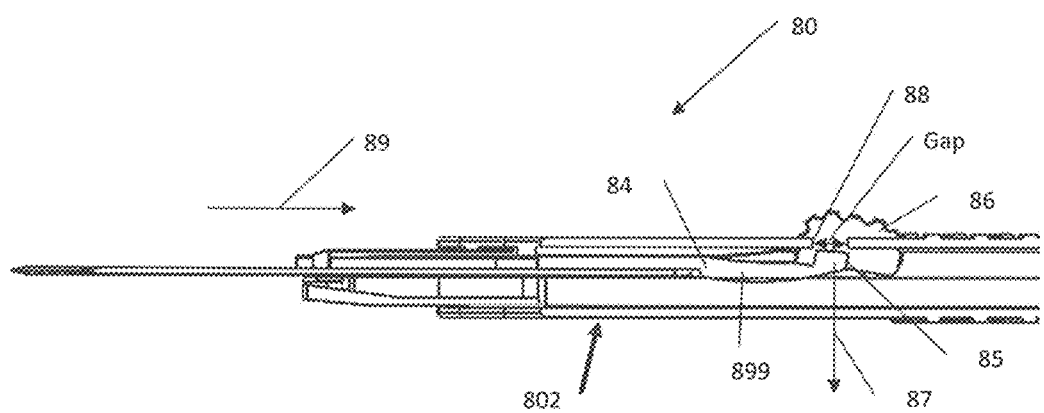
FIG. 8B is a section view of the safety scalpel when the blade is in a cutting position in which the blade holder is activated through an activation member.

FIG. 8A is a section view of a safety scalpel 80 in a cutting condition when a blade 82 of the safety scalpel 80 is in a cutting position upon activation of a blade holder 81 from a pre-cutting state. FIG. 8B is a section view of the safety scalpel 80 being retracted from the cutting condition to a pre-cutting condition. The safety scalpel 80 comprises a handle 800 and a blade cartridge 802 releasably attached to the handle 800. The blade cartridge 802 comprises a blade holder 81 in communication with a blade 82. The blade 82 is extended in a cutting position upon activation of the blade holder 81. The blade holder 81 may comprise an activation member 899 having a resilient portion 84 and a button 86 provided on the resilient portion 84. The resilient portion 84 may include a latch portion 85 adapted to be received in an opening 88 of the blade cartridge 802.

Referring to FIG. 8B, the resilient portion 84 may be configured to, or be made of a material with elastic properties which enable the activation member 899 to deflect in a direction 87 so as to enable the blade 82 to be retracted in a direction of travel 89. The direction 87 in which the activation member 899 may be deflected may be substantially perpendicular to the direction of travel 89. When the activation member 899 is deflected in a direction 87, the latch portion 85 may be movable between a first position (FIG. 8A) in which it is engaged with and on a top surface of the blade cartridge 802 and a second position (FIG. 8B) in which it is below the top surface to enable sliding of the blade holder 81 and the blade 82.

Figure 8C:
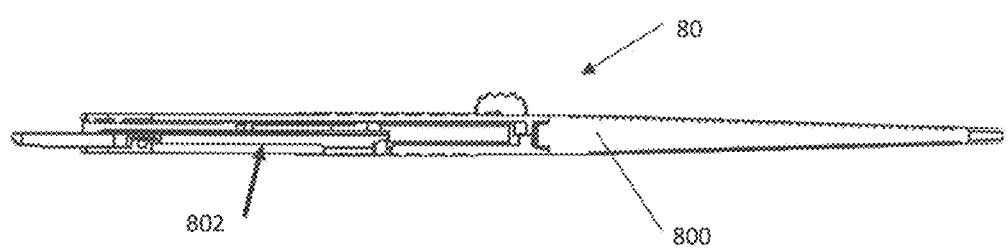
FIG. 8C is a section view of the safety scalpel in a stowed position in a pre-cutting state of a blade holder.

FIG. 8C is a section view of the safety scalpel 80 in a stowed configuration and in a pre-cutting condition wherein the blade 82 is retracted to a stowed position and the activation member 899 is at a third position along the top surface of the blade cartridge 802.

Figure 9A:
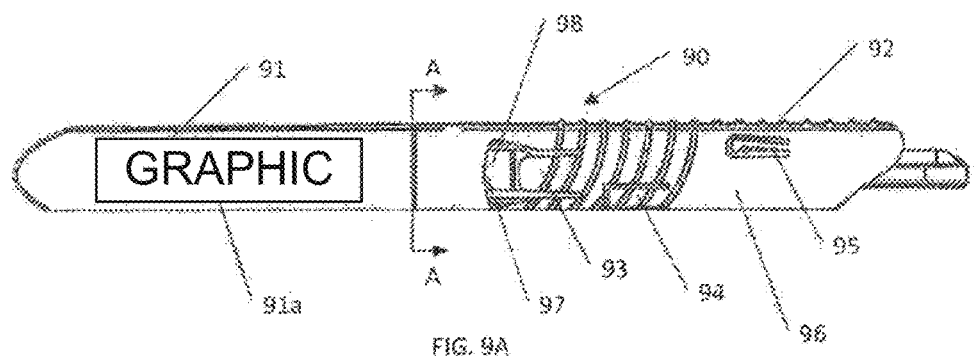
FIG. 9A is a rear perspective view of a safety scalpel in a stowed position in a pre-cutting state of a blade holder.

FIG. 9A is a rear perspective view of a safety scalpel 90 when a blade (Not shown in FIG. 9A) of the safety scalpel 90 is in a stowed position. The safety scalpel 90 has a scalpel handle 91 and a blade cartridge 92 releasably attached to the handle 91. In the present example, the blade cartridge 92 comprises the blade (Not shown in FIG. 9A), a housing 96, and a blade holder 98. The blade cartridge 92 has a resilient lock member 95 disposed within the housing 96 wherein the resilient lock member 95 is in an unbiased condition when the blade (Not shown in FIG. 9A) is in the stowed position. The blade cartridge 92 may also include a blade lock mechanism configured to lock the blade (not shown in FIG. 9A) residing in the safety scalpel 90 before the handle 91 is assembled to the blade cartridge 92 to form the safety scalpel 90. The blade cartridge 92 may comprise a resilient release tab 93 for engaging the handle 91 to lock the blade cartridge 92 to the handle 91. The handle 91 may include a cut-out feature 97 formed in a rear surface of a blade receiving portion of the handle 91. The cut-out feature 97 may be a sloped recess 97 configured to be inclined at an angle relative to a rear surface of the handle 91 to enable ease of disassembly of the blade cartridge 92 in a stowed position in a pre-cutting state of the blade holder 98. A graphic 91a such as a trade mark or a logo may be provided on a handle portion of the handle 91.

Figure 9B:
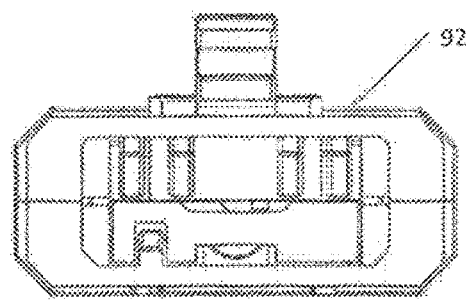
FIG. 9B is a section view of the safety scalpel of FIG. 9A.

FIG. 9B is a section AA view of the safety scalpel 90 of FIG. 9A with the handle 91 and the blade cartridge 92.

Figure 9C:
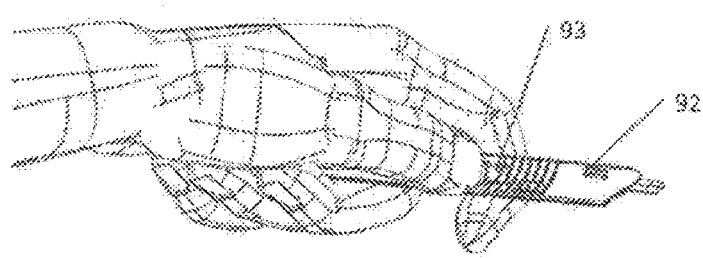
FIG. 9C is an illustrative view of a method of releasing a blade cartridge from the safety scalpel of FIG. 9A.
Figure 9D:
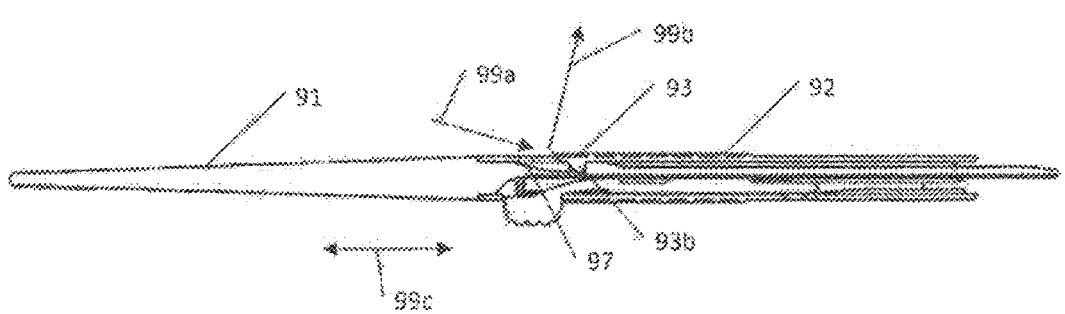
FIG. 9D is a side section view of the safety scalpel.

FIG. 9C is an illustrative view of a method of releasing the blade cartridge 92 from the handle 91. FIG. 9D is a side section view of the safety scalpel 90 showing a force application in directions 99a and 99b to release or detach the blade cartridge 92 from the handle 91 resulting in disassembly of the safety scalpel 90.

As seen in the direction 99b, a motion to apply a force in the direction 99b at the release tab 93 is perpendicular to a direction of movement 99c of a blade holder (Not shown in FIG. 9C). This may be regarded as a safety mechanism of the safety scalpel 90 to prevent inadvertent release of the blade cartridge 92 employed during normal use of the scalpel 90.

Referring to FIGS. 9A and 9D, the sloped recess 97 in the handle 91 may be adapted to have a locating surface for guiding the release tab 93 in the cartridge into a tab receiving aperture on the handle 91. The tab receiving aperture may be similar to the tab receiving aperture 21 of the handle 2 in FIG. 5A. For example, the handle 91 may have a notch-shaped feature and a longitudinal groove feature provided on the blade receiving portion to guide a protrusion 93b of the release tab 93 into the tab receiving aperture to releasably lock the blade cartridge 92 to the handle 91. Further, the sloped recess 77 may be configured to facilitate single-handed release of the blade cartridge 92 such that the user may not require a tool to detach the blade cartridge 92 from the handle 91.

Further embodiments of a safety scalpel with a replaceable blade cartridge will be described below with reference to FIGS. 10A to 24B. It is to be understood by those skilled in the art that the further embodiments may be configured to have components similar to the components described in FIGS. 1 to 9D, and such components will not be described. Similarly, it is to be understood that the mention of one or more components in a device (component, part) or an assembly (system) does not preclude the presence of additional components or intervening component s between those components expressly identified.

Figure 10A:
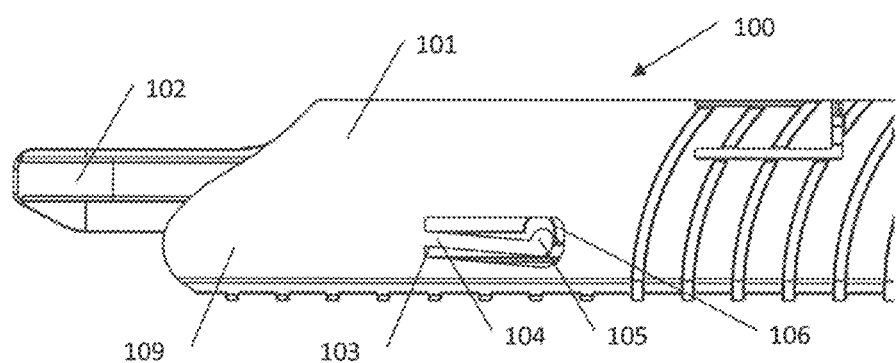
FIG. 10A is a rear view of a safety scalpel in a stowed position in a pre-cutting state of a blade holder.

FIG. 10A is a rear view of a safety scalpel 100 when a blade (107 in FIG. 10B) of the safety scalpel 100 is in a stowed position. The safety scalpel 100 has a handle 102 releasably attached to a blade cartridge assembly 101. The blade cartridge assembly 101 includes the blade (107 in FIG. 10B), a housing 109, and a blade holder (108 in FIG. 10B) in communication with the blade (107 in FIG. 10B). A resilient lock mechanism or member 103 may be provided within the housing when the blade holder (108 in FIG. 10B) is in a pre-cutting state as shown in FIG. 10A. The resilient lock mechanism or member 103 may include a resilient arm 104 and a latch member 105 adapted to engage a locking aperture 106 of the handle 102.

Figure 10B:
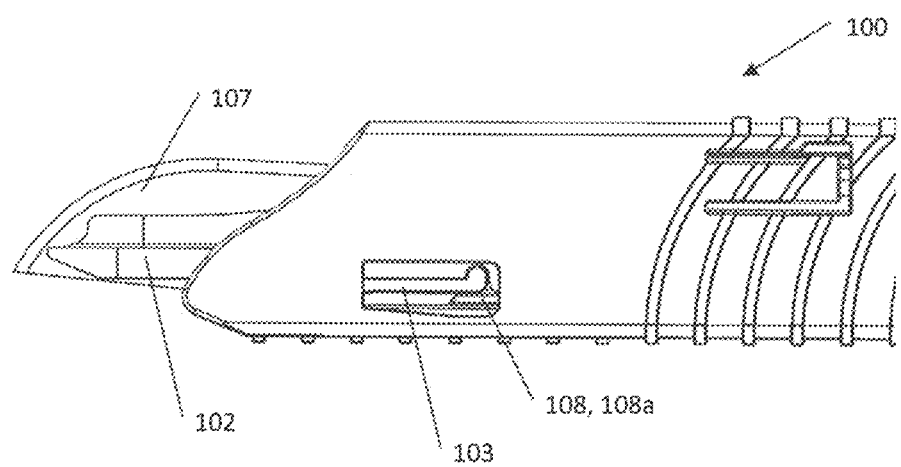
FIG. 10B is a rear view of the safety scalpel when a blade is in a cutting position upon activation of a blade holder.

FIG. 10B is a rear view of the safety scalpel 100 in the process of moving from a stowed configuration to a cutting configuration wherein the blade 107 is in a cutting position upon activation of the blade holder 108 from a pre-cutting state of the blade holder 108. Referring to FIG. 10B, a blade holder 108 may be adapted to engage with the resilient arm 104 to move the latch member 105 into the locking aperture 106 to lock the blade cartridge assembly 101 to the handle 102 when the blade 107 reaches the cutting position. For example, the blade holder 108 may include a wall portion 108a adapted to slidably engage the resilient arm 104 of the resilient lock mechanism 103.

Figure 11A:
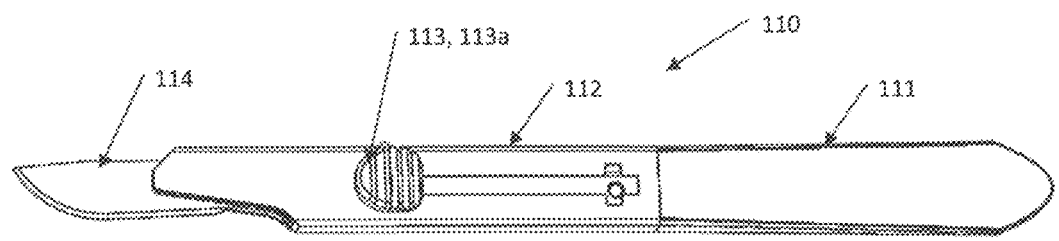
FIGS. 11A to 12C are perspective and section views illustrating embodiments of activation members for safety scalpels.
Figure 11B:
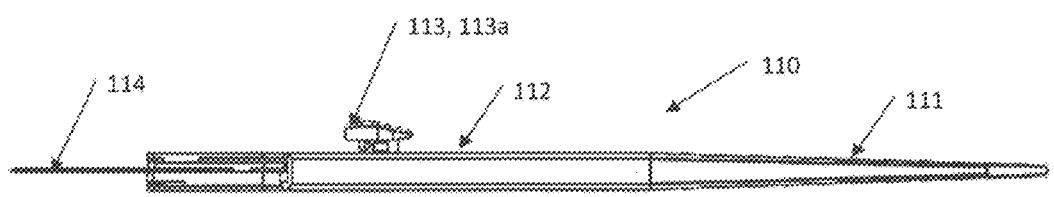

FIG. 11A is a top perspective view of a safety scalpel 110 when a blade 114 of the safety scalpel 110 is in a cutting position upon activation of a blade holder 113 from a pre-cutting state of the blade holder 113. FIG. 11B is a side section view of the safety scalpel 110. The safety scalpel 110 comprises a handle 111, and a blade cartridge 112 releasably attached to the handle 111. The blade cartridge 112 may include a blade holder 113 in communication with a blade 114. The blade holder 113 further comprises an activation member 113a adapted to allow the blade holder 113 to slide relative to a housing of the blade cartridge 112, and the handle 111.

Figure 12A:
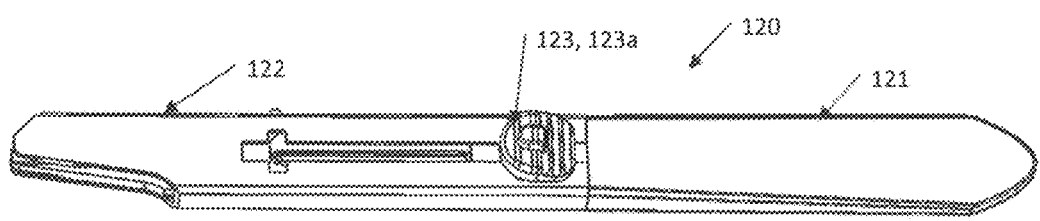
Figure 12B:
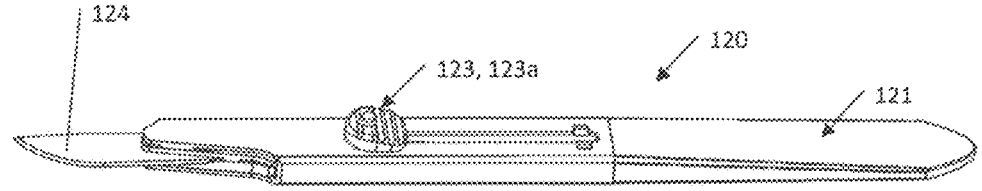
Figure 12C:
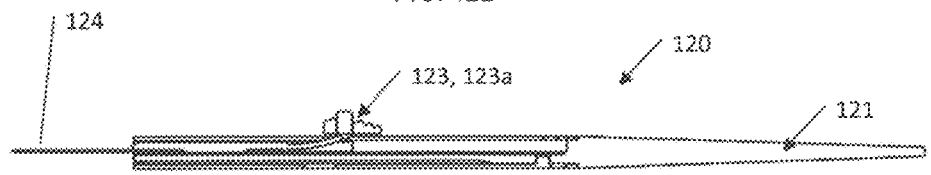

FIG. 12A is a top perspective view of a safety scalpel 120 when a blade (124 in FIG. 12B) of the safety scalpel 120 is in a stowed position. FIG. 12B is another top perspective view of the safety scalpel 120 when the blade 124 is in a cutting position upon activation of a blade holder 123 and FIG. 12C is a side section view of FIG. 12B. The safety scalpel 120 comprises a handle 121, and a blade cartridge 122 releasably attached to the handle 121. The blade cartridge 122 may include the blade holder 123 in communication with the blade 124. The blade holder 123 further comprises an activation member 123a adapted to allow the blade holder 123 to slide relative to a housing of the blade cartridge 122, and the handle 121.

Figure 13A:
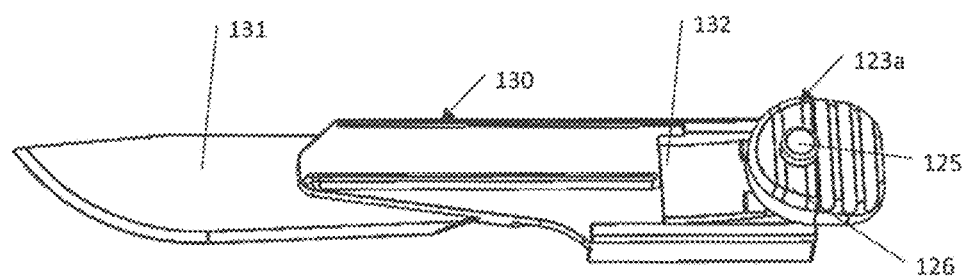
FIG. 13A is a perspective view of a blade holder with a blade.
Figure 13B:
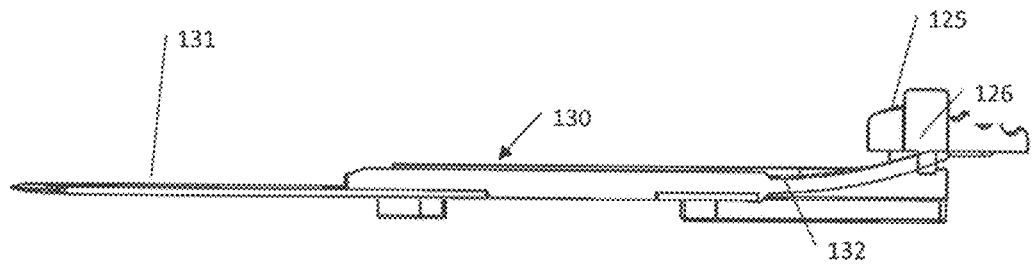
FIG. 13B is a section view of the blade holder of FIG. 13A.

FIG. 13A is a top perspective view of a blade holder 130 having the activation member 123a. A blade 131 is attached to the blade holder 130. FIG. 13B is a side section view of FIG. 13A. The activation member 123a may include a first button 125 embedded (or embedded button) in a second button 126 which is larger in size relative to the first button. The first button 125 may be configured to actuate the blade holder 130. The second button 126 may be formed to flush or in the same plane with the cartridge 122. The first button 125 may be directly connected to the blade holder 130. The activation member 123a may include a resilient section 132 for allowing the activation member 123a to be deflected to allow sliding of the blade holder 130 along the handle (Not shown in FIG. 13A but similar to 121 in FIGS. 12A, 12B and 12C).

Figure 14A:
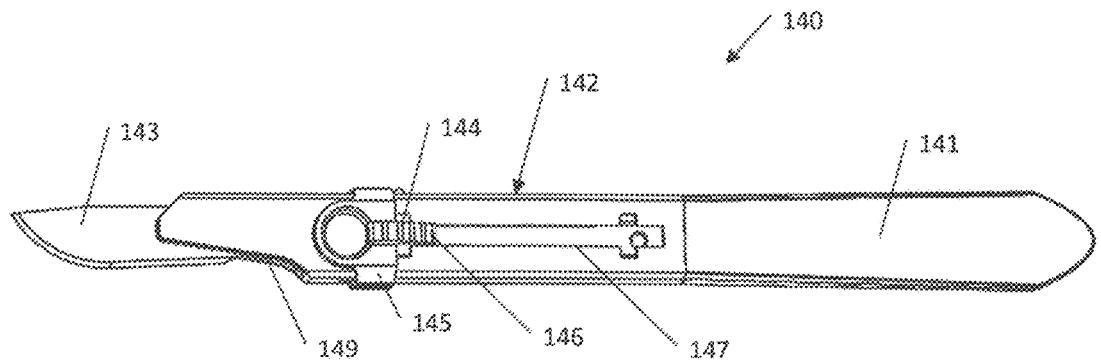
FIG. 14A is a top perspective view of a safety scalpel.

FIG. 14A is a top perspective view of a safety scalpel 140 according to another embodiment. The safety scalpel 140 comprises a handle 141, and a blade cartridge 142 releasably attached to the handle 141. The blade cartridge 142 may include a blade holder 149 in communication with a blade 143, and an activation mechanism 144 adapted to allow the blade holder 149 to slide relative to a housing of the blade cartridge 142, and the handle 141.

Figure 14B:
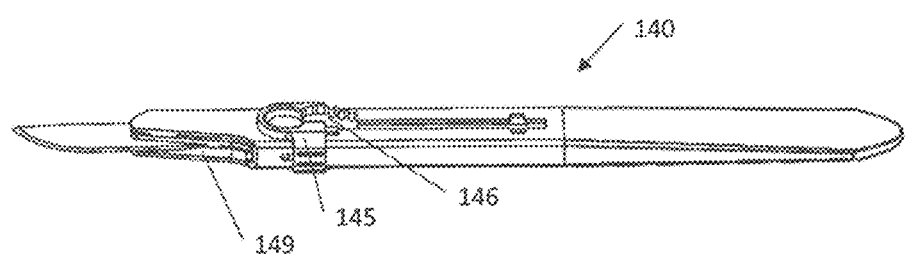
FIG. 14B is a top perspective view of the safety scalpel of FIG. 14A.
Figure 14C:
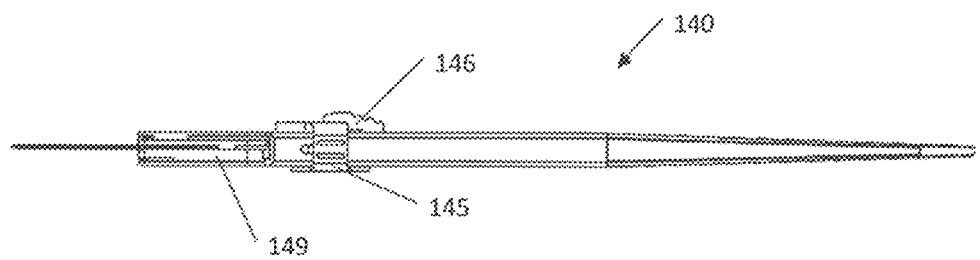
FIG. 14C is a side view of the safety scalpel of FIG. 14A.

FIG. 14B is a side section view of FIG. 14A. The activation mechanism 144 may include a button guard 145 configured to slide under a button 146 such that the activation mechanism 144 locks the blade holder 149 during use. A sliding action may also actuate the activation mechanism 144. For example, the activation mechanism 144 may be configured to slide linearly in a groove 147 adapted to receive the activation mechanism 144. FIG. 14C is a side view of FIG. 14A.

Figure 15A:
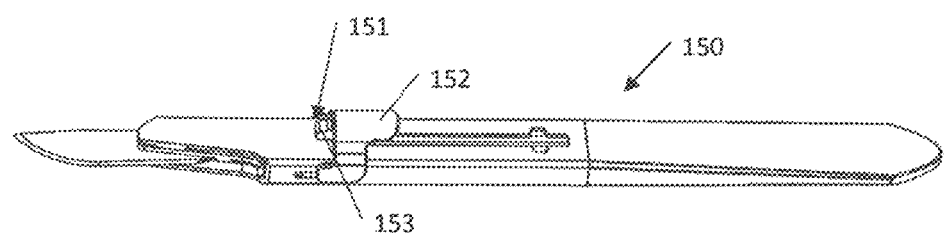
FIG. 15A is a top perspective view of a safety scalpel.
Figure 15B:
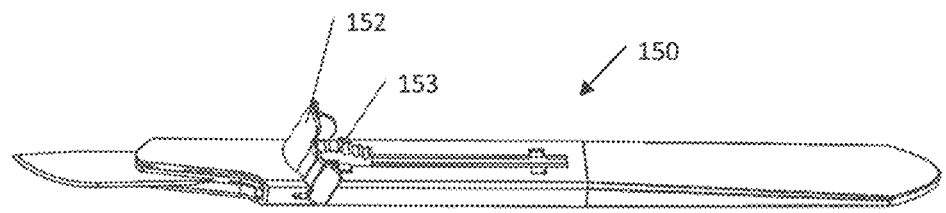
FIG. 15B is a side section view of the safety scalpel of FIG. 15A.

FIG. 15A is a top perspective view of a safety scalpel 150 having an activation mechanism 151. FIG. 15B is a side section view of FIG. 15A. The safety scalpel 150 is similar in configuration to the safety scalpel 140 of FIG. 14A. For the safety scalpel 150, an activation mechanism 151 of it may include a flip guard 152 adapted to cover a button 153 during use.

Figure 16A:
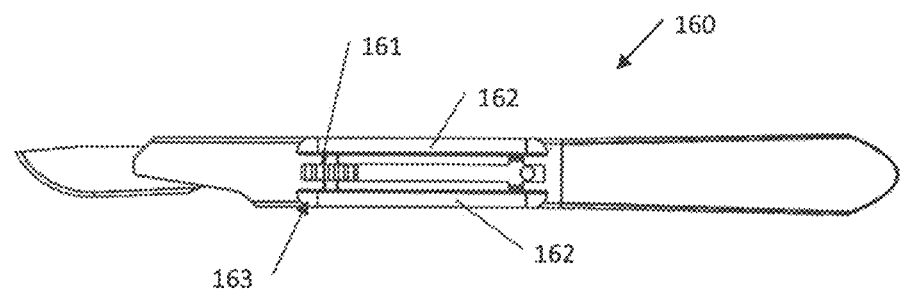
FIG. 16A is a top perspective view of a safety scalpel.
Figure 16B:
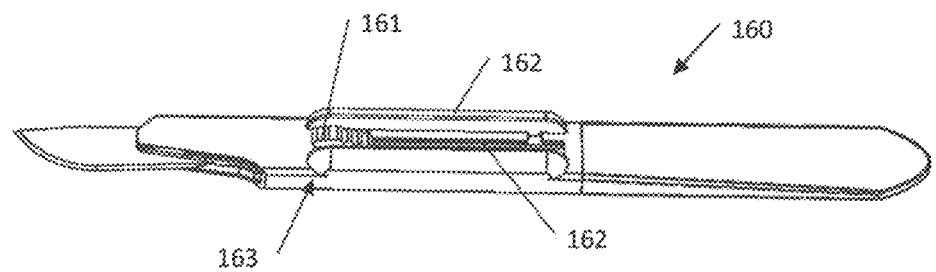
FIG. 16B is a top perspective view of the safety scalpel of FIG. 16A.

FIG. 16A is a top perspective view of a safety scalpel 160 having an activation mechanism 161 adapted to slide within a plurality of side projections 162 provided on a blade cartridge 163 of the safety scalpel 160. FIG. 16B is a side section view of FIG. 16A. The side projections 162 function as a guard against inadvertent activation of the activation mechanism 161 because a user would be required to execute purposeful motion to actuate the activation mechanism 161.

Figure 17A:
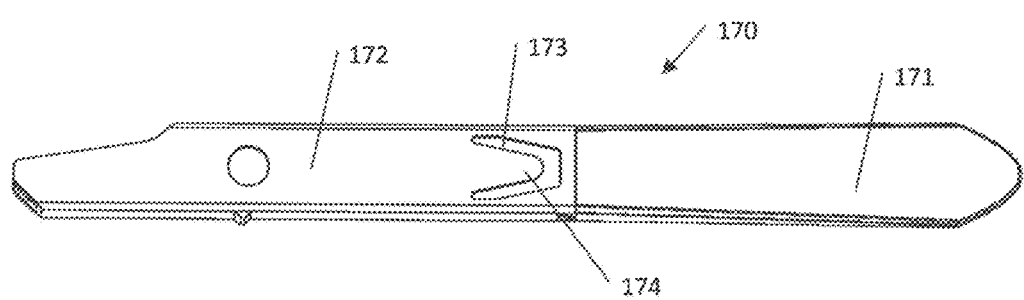
FIG. 17A is a top perspective view of a safety scalpel having a cartridge release mechanism.
Figure 17B:
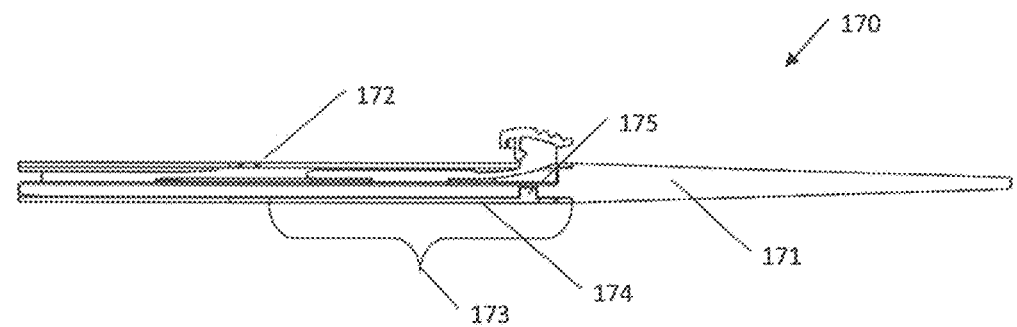
FIG. 17B is a side section view of the safety scalpel of FIG. 17A.

FIG. 17A is a top perspective view of a safety scalpel 170 having a handle 171 and a blade cartridge 172 releasably attached to the handle 171 and having a cartridge release mechanism 173. FIG. 17B is a side section view of FIG. 17A. For example, the cartridge release mechanism 173 may comprise a resilient portion 174 and a catch 175 extending from the resilient portion 174. When the blade cartridge 172 is attached to the handle 171, the catch 175 engages with the handle 171 through a corresponding recess of the handle 171. When the resilient portion 174 is moved in a direction perpendicular to a direction of sliding of the blade (not shown) of the safety scalpel, the resilient portion 174 deflects and the catch 175 disengages from the corresponding recess of the handle 171 to release the cartridge 172 from the handle 171.

Figure 18A:
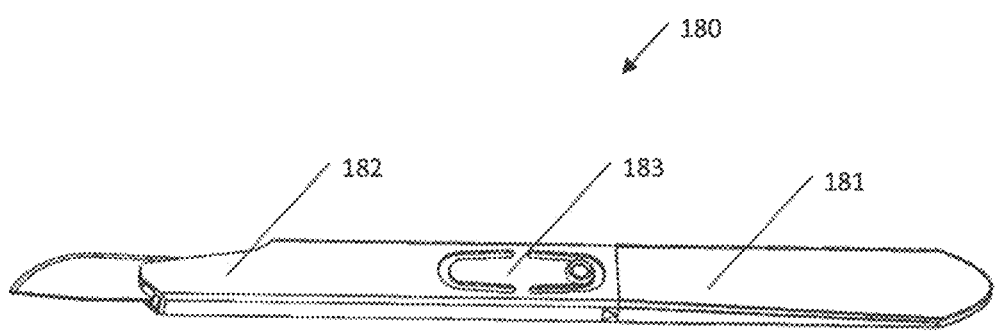
FIG. 18A is a top perspective view of a safety scalpel having a cartridge release mechanism.
Figure 18B:
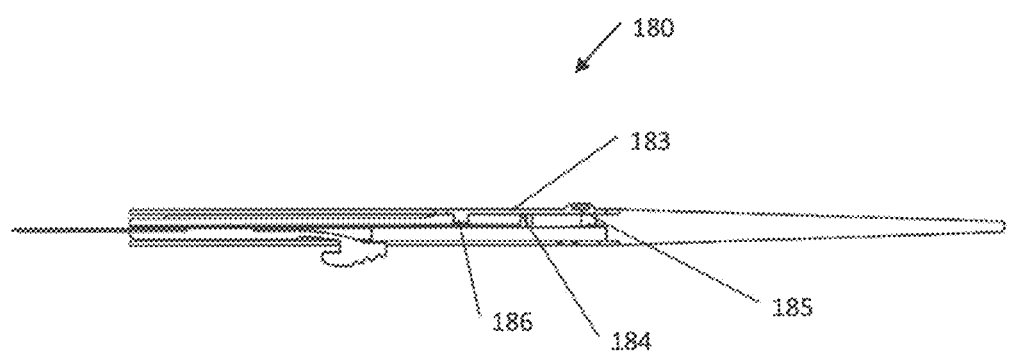
FIG. 18B is a side section view of the safety scalpel of FIG. 18A.

FIG. 18A is a top perspective view of a safety scalpel 180 having a handle 181 and a blade cartridge 182 releasably attached to the handle 181 and having a cartridge release mechanism 183. FIG. 18B is a side section view of FIG. 18A.

The cartridge release mechanism 183 may comprises a resilient member 184 having an activation member 185 located at one end and a catch member 186 located at another end. The catch member 186 may be arranged to engage with the handle 181 through a corresponding recess of the handle 181. When the activation member 185 is pressed in a direction towards a surface of the handle 181, the resilient portion 185 may be adapted to deflect and allow the catch 186 to be disengaged from the corresponding recess of the handle 181 to release the cartridge 182 from the handle 181.

Figure 19A:
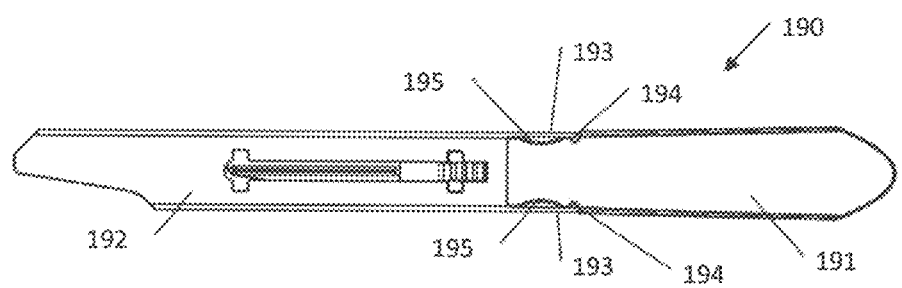
FIG. 19A is a top view of a safety scalpel having a cartridge release mechanism.
Figure 19B:
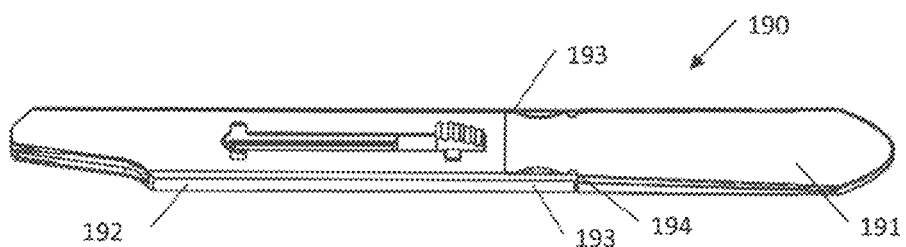
FIG. 19B is a top perspective view of the safety scalpel of FIG. 19A.

FIG. 19A is a top perspective view of a safety scalpel 190 having a handle 191 and a blade cartridge 192 releasably attached to the handle 191 and having a cartridge release mechanism. FIG. 19B is a side section view of FIG. 19A. The cartridge release mechanism may comprises snap features 193 located on opposing sides of the housing, wherein the snap features 193 are adapted to releasably attach the blade cartridge 192 to the handle.

For example, each of the snap features 193 may comprise a resilient portion 193 and a catch 194 extending from the resilient portion 193. When the blade cartridge 192 is attached to the handle 191, the catch 194 engages with the handle 191 through a corresponding recess of the handle 191. When each of the snap features 193 is pressed at the resilient portion 193 in a direction toward a recess 195 of the handle 191, the resilient portion 193 deflects and the catch 194 disengages from the corresponding recess of the handle 191 to release the cartridge 192 from the handle 191.

Figure 20A:
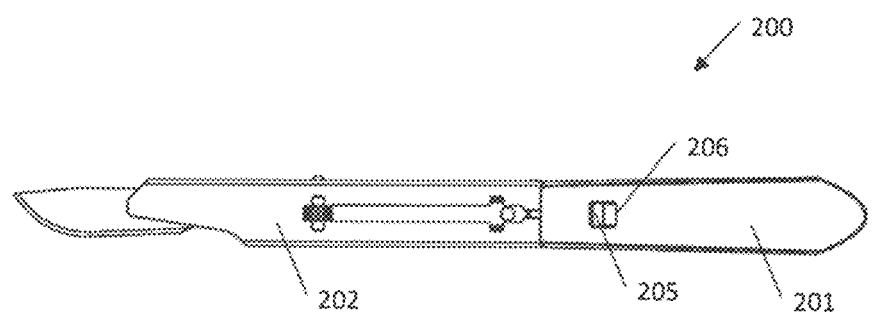
FIG. 20A is a top view of a safety scalpel having a cartridge release mechanism.
Figure 20B:
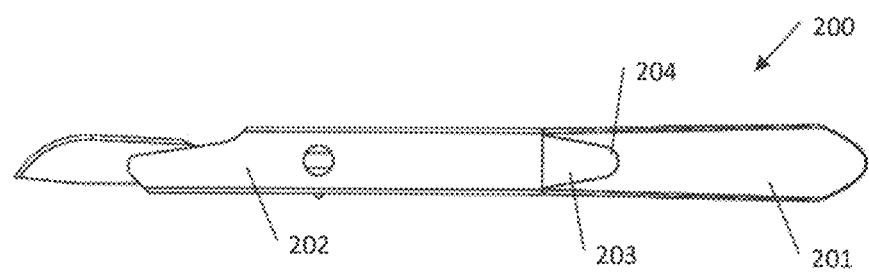
FIG. 20B is a rear view of the safety scalpel of FIG. 20A.
Figure 20C:
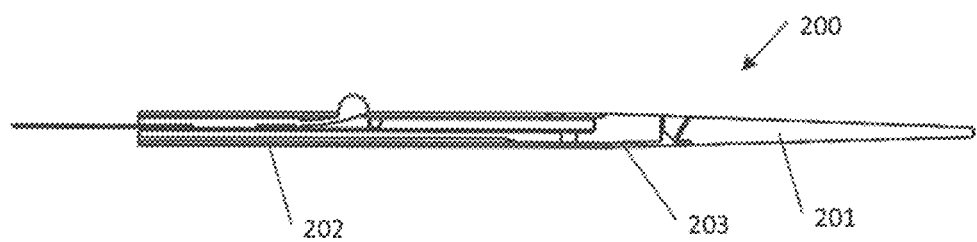
FIG. 20C is a side section view of the safety scalpel of FIG. 20A.

FIG. 20A is a top perspective view of a safety scalpel 200 having a handle 201 and a blade cartridge 202 releasably attached to the handle 201 by having a cartridge release mechanism 203. FIG. 20B is a rear view of the safety scalpel 200 and FIG. 20C is a side section view of the safety scalpel 200. For example, the cartridge release mechanism 203 may comprise a resilient portion 204 and a catch 205 extending from the resilient portion 204. When the blade cartridge 202 is attached to the handle 201, the catch 205 engages with the handle 201 through a corresponding recess 206 of the handle 206.

Figure 21A:
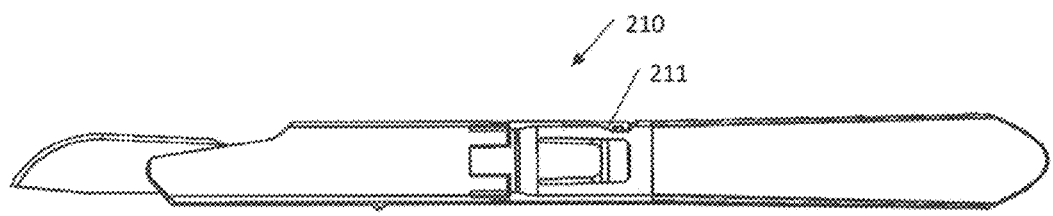
FIG. 21A is a rear perspective view of a safety scalpel having a cartridge release mechanism.
Figure 21B:
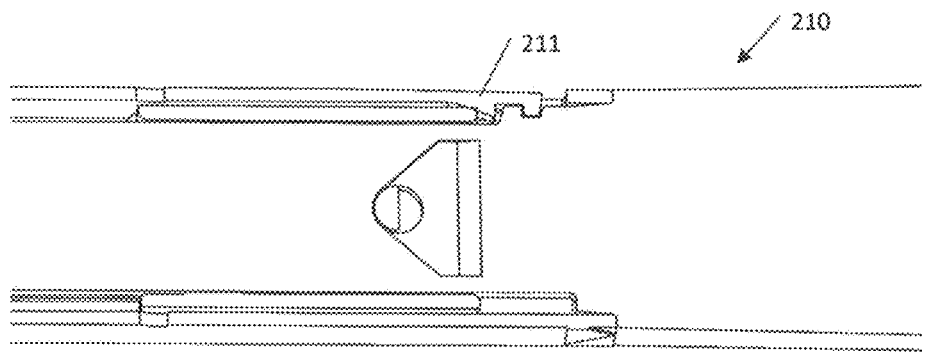
FIG. 21B is a detailed perspective view of the safety scalpel of FIG. 21A.

FIG. 21A is a rear perspective view of a safety scalpel 210 having a cartridge release mechanism 211. FIG. 21A is a detailed view of the safety scalpel 210.

Figure 22A:
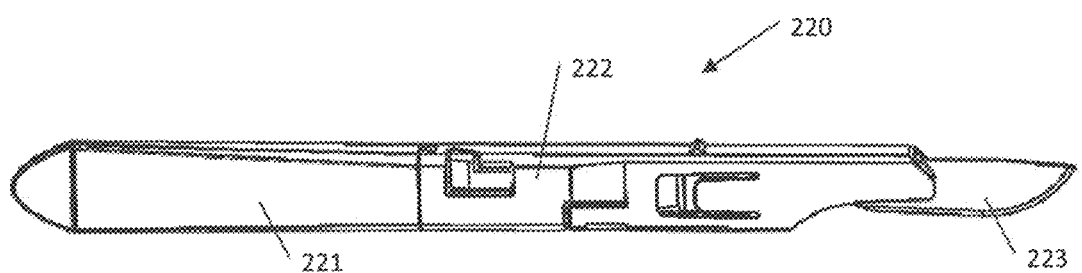
FIG. 22A is a rear perspective view of a safety scalpel.
Figure 22B:
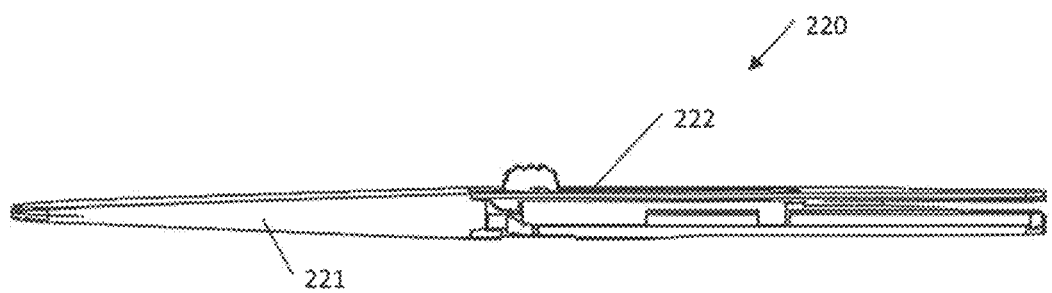
FIG. 22B is a left side view of the safety scalpel of FIG. 22A.
Figure 22C:
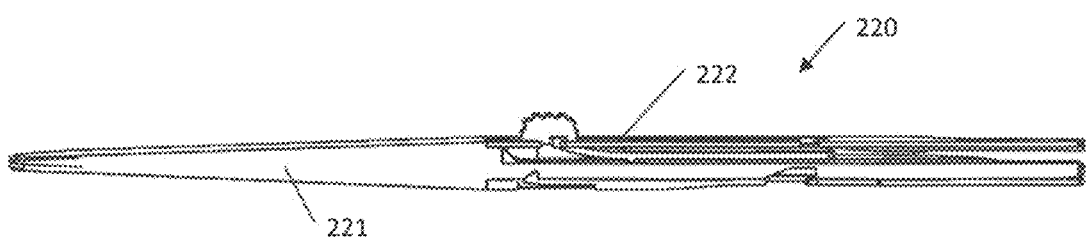
FIG. 22C is a right side view of the safety scalpel of FIG. 22A.

FIG. 22A is a rear view of a safety scalpel 220 when a blade of the safety scalpel 223 is in a cutting position upon activation of a blade holder (Not shown in FIG. 22A), wherein the safety scalpel 220 has a handle 221 and a blade cartridge 222 releasably attached to the handle 221. FIG. 22B is a left side view of the safety scalpel 220 and FIG. 22C is a right side view of the safety scalpel 220.

Figure 23A:
FIG. 23A is a side section view of a safety scalpel.
Figure 23B:
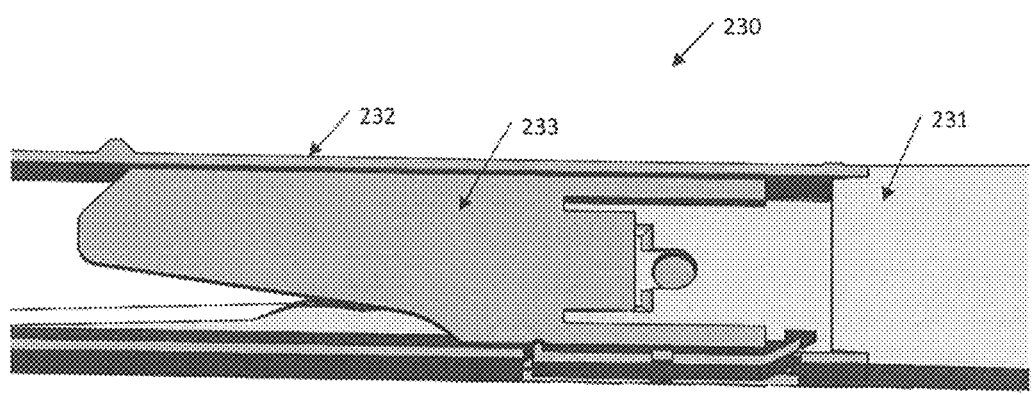
FIG. 23B is a rear perspective view of the safety scalpel.
Figure 23C:
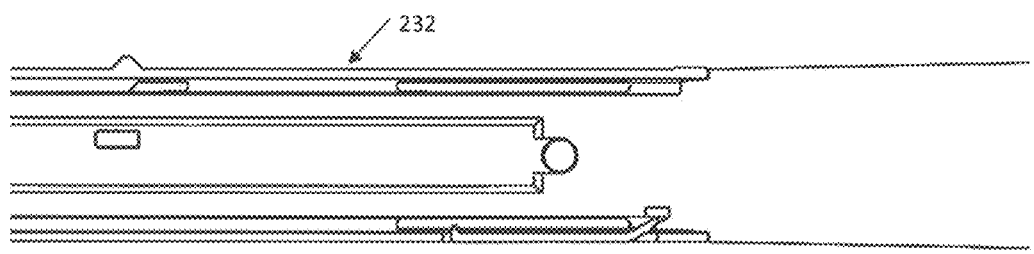
FIG. 23C is a rear section view of the safety scalpel with the blade holder removed.

FIG. 23A is a side section view of a safety scalpel 230 having a handle 231 and a blade cartridge 232 releasably attached to the handle 231. FIG. 23B is a rear view of the safety scalpel 230 showing a blade holder 233 of the blade cartridge 232. FIG. 23C is a rear view of the safety scalpel 230 with the blade holder 233 removed. In an example, the safety scalpel 230 may comprise a handle ramp (not shown) provided on the handle 231, wherein the handle ramp is adapted to push on a housing ramp (not shown) upon insertion of the handle, to move the housing ramp out of an aperture in the blade holder 233. The housing ramp may be provided on the blade cartridge 232 and similar in configuration as the ramp 66 as shown in FIG. 6A except that instead of abutting the blade holder 233, the housing ramp engages with an aperture in the blade holder 233.

Figure 24A:
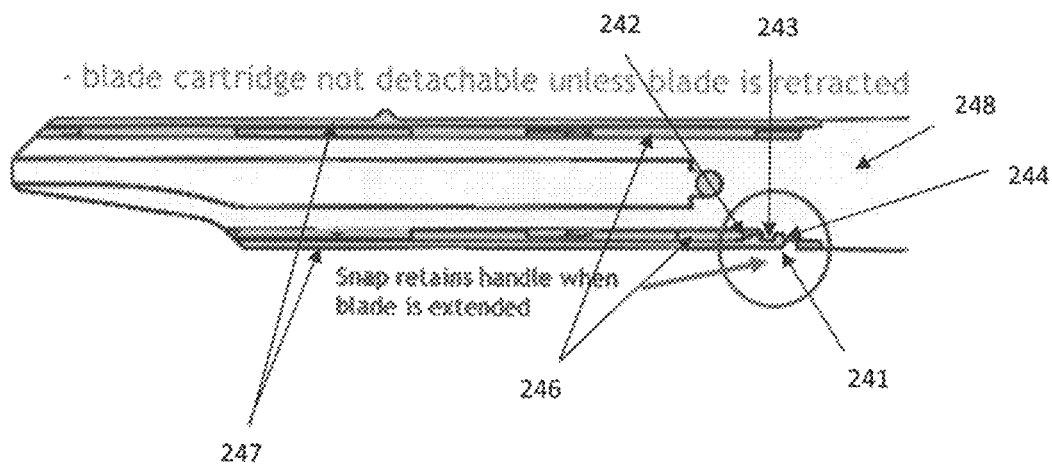
FIG. 24A and FIG. 24B are rear section views of a safety scalpel having a handle and a blade cartridge releasably attached to the handle.
Figure 24B:
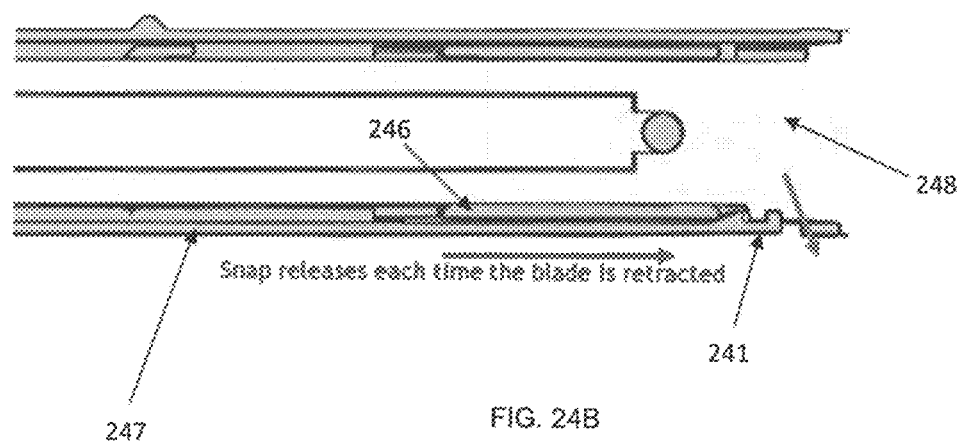

FIG. 24A and FIG. 24B are rear section views of an example safety scalpel 240 having a handle 248. A blade cartridge 247 on an outermost surface is releasably attached to the handle 248. A blade holder 246 holding a blade (not shown in FIG. 24A) is disposed between the the blade cartridge 247 and the handle 248. The blade holder 246 is configured to allow the blade (not shown in FIG. 24A) to extend between a stowed position in a pre-cutting state of the blade holder 246 and a cutting position upon activation of the blade holder 246. The blade holder 246 is in the pre-cutting state when the blade (not shown in FIG. 24A) is in the stowed position. A releasable scalpel snap 241 (or resilient lock member) is disposed within a housing of the blade cartridge 247. It is appreciated that the snap 241 can be separately mounted to the housing of the blade cartridge 247 instead of being integral in another example.

The snap 241 is adapted to lock to the handle 248 in a default configuration (or unbiased condition) where the blade holder 246 is extended to set the blade (not shown in FIG. 24A) in the cutting position. The snap 241 is adapted to disengage from the handle 248 when the blade holder 246 is retracted to set the blade (not shown in FIG. 24A) in the stowed position. As the blade holder 246 retracts, it will slide to abut against or engage the snap 241 and cause the snap 241 to disengage from the handle. It is appreciated that the portion of the blade holder 246 abutting against the snap 241 can also be said to be an activation member as discussed in the present disclosure. After blade retraction, removal of the blade cartridge 247 from the handle 248 is allowed as the snap 241 disengages (or unlocks) from the handle 248. During blade extension to the cutting position, the blade holder 246 slides away from the snap 241 and no longer abuts the snap 241. This causes the snap 241 to revert back to lock the handle 248.

In the present example, an end portion of the snap 241 is in a form of a protrusion 244 protruding in a direction towards the handle 248. The protrusion 244 is configured to engage a locking aperture of the handle 248 when the snap 241 is locked to the handle 248. The snap has a recess 243 located adjacent to the protrusion 244 for receiving a locking protrusion of the handle 248. Furthermore, the snap 241 has a sloped protrusion 242 located adjacent to the recess 243 and away from the location of the protrusion 244. The sloped protrusion 242 has a sloped surface tapering away from the protrusion 244.

With reference to FIG. 24B, during blade retraction, the blade holder 246 slides toward the sloped protrusion 242 and gradually exerts force on the sloped protrusion 242 beginning from the tapered end of sloped surface of the sloped protrusion 242. As the retracting blade holder 246 slides further along the sloped surface, the sloped protrusion 242, the recess 243 and the protrusion 244 of the snap 241 will be pushed away to disengage (or unlock) and lose contact with the handle 248. When the snap 241 no longer contacts the handle 248, the blade cartridge 247 can be removed from the handle 248 by detaching (in this case, through sliding) it away from the handle in the direction of the extension of the blade (not shown in FIG. 24B).

With reference to FIG. 24A, during blade extension, the blade holder 246 slides away from the sloped protrusion 242 of the snap 241 and progressively releases the force exerted on the sloped surface of the slope protrusion 242. In this manner, the recess 243 and the protrusion 244 of the snap 241 will revert back to engage (or lock) the locking protrusion and the locking aperture of the handle 248 respectively such that the blade cartridge 247 cannot be removed from the handle 248 by forces pulling it in the direction of the extension of the blade (not shown in FIG. 24A).

Figure 25A:
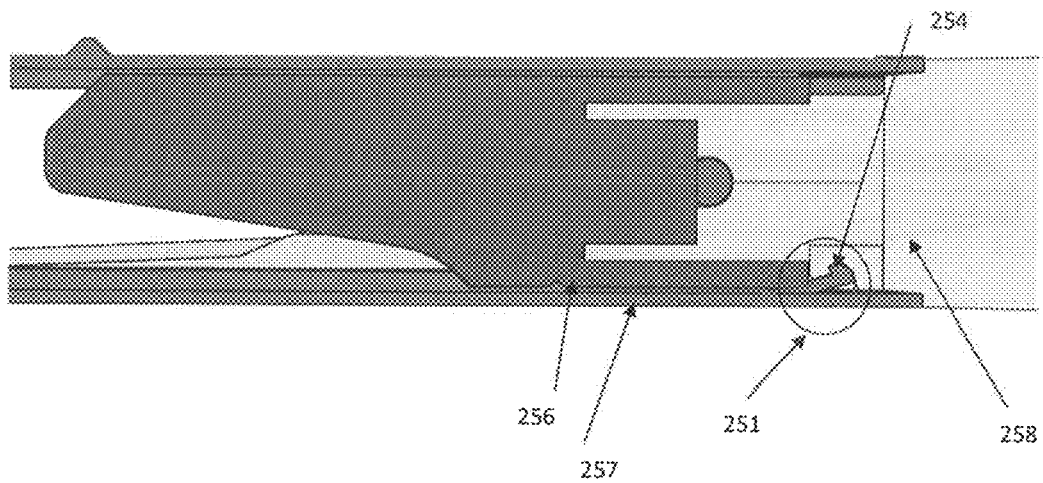
FIG. 25A and FIG. 25B are rear section views of a safety scalpel having a handle and a blade cartridge releasably attached to the handle.
Figure 25B:
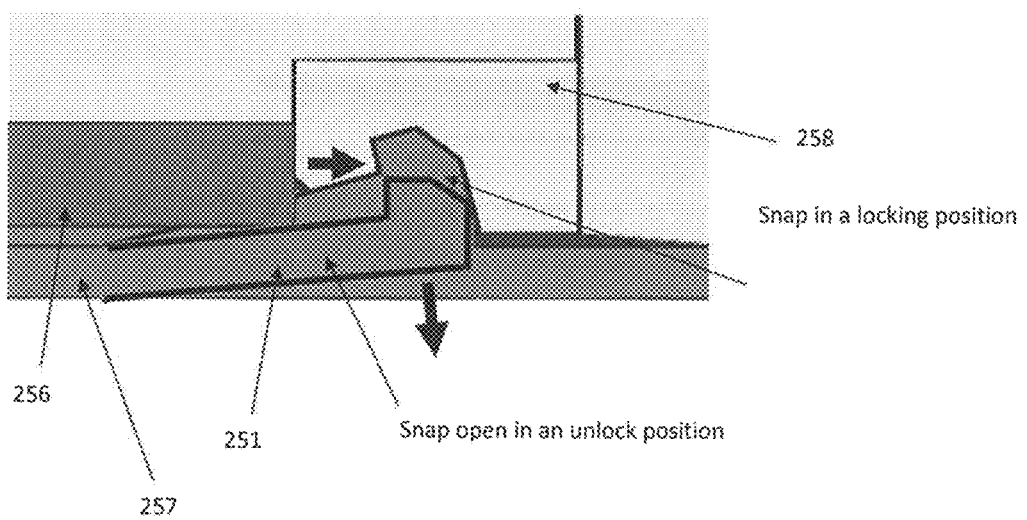

FIG. 25A and FIG. 25B are rear section views of an example safety scalpel 251 having a handle 258. A blade cartridge 257 on an outermost surface is releasably attached to the handle 258. A blade holder 256 holding a blade (not shown in FIGS. 25A and 25B) is disposed between the blade cartridge 257 and the handle 258. The blade holder 256 is configured to allow the blade (not shown in FIG. 25A and FIG. 25B) to extend between a stowed position in a pre-cutting state of the blade holder 256 and a cutting position upon activation of the blade holder 256. The blade holder 256 is in the pre-cutting state when the blade (not shown in FIG. 25A and FIG. 25B) is in the stowed position. A releasable scalpel snap 251 (or resilient lock member) is disposed within a housing of the blade cartridge 257. It is appreciated that the snap 251 can be separately mounted to the housing of the blade cartridge 257 instead of being integral in another example.

The snap 251 is adapted to lock to the handle 258 in a default configuration (or unbiased condition) where the blade holder 256 is extended to set the blade in the cutting position. The snap 251 is adapted to disengage from the handle 258 when the blade holder 256 is retracted to set the blade (not shown in FIG. 25A and FIG. 25B) in the stowed position. As the blade holder 256 retracts, it will slide to abut against or engage the snap 251 and cause the snap 251 to disengage from the handle. It is appreciated that the portion of the blade holder 256 abutting against the snap 251 can also be said to be an activation member as discussed in the present disclosure. After blade retraction, removal of the blade cartridge 257 from the handle 258 is allowed as the snap 251 disengages (or unlocks) from the handle 258. During blade extension to the cutting position upon activation of the blade holder 256, the blade holder 256 slides away from the snap 251 and no longer abuts the snap 251. This causes the snap 251 to revert back to lock the handle 258.

In the present example, an end portion of the snap 251 is in a form of a protrusion 254 protruding in a direction towards the handle 258. The protrusion 254 acts like a hook that is configured to engage a locking aperture of the handle 258 when the snap 251 is locked to the handle 258. The locking aperture of the handle 258 is located further into a main body of the handle 258 compared to the handle 248 of the example described with reference to FIGS. 24A and 24B. In the default position, the snap 251 is angled away from the blade cartridge 257 and towards the handle. As the snap 251 is angled, a slope tapering towards the blade cartridge 257 is formed.

With reference to FIG. 25B, during blade retraction, the blade holder 256 slides toward the angled snap 251 and gradually exerts force on the angled snap 251 beginning from the tapered end of angled snap 251. As the retracting blade holder 256 slides further along a sloped surface of the angled snap 251, the protrusion 254 will be pushed away to disengage (or unlock) and lose contact with the handle 258. When the snap 251 no longer contacts the handle 258, the blade cartridge 257 can be removed from the handle 258 by detaching (in this case, through sliding) it away from the handle 258 in the direction of the extension of the blade (not shown in FIG. 25A and FIG. 25B).

With reference to FIG. 25A, during blade extension, the blade holder 256 slides away from the angled snap 251 and progressively releases the force exerted on the angled snap 251. In this manner, the protrusion 254 of the snap 251 will return to engage (or lock) the locking aperture of the handle 258 such that the blade cartridge 257 cannot be removed from the handle 258 by forces pulling it in the direction of the extension of the blade (not shown in FIG. 25A and FIG. 25B).

Figure 26A:
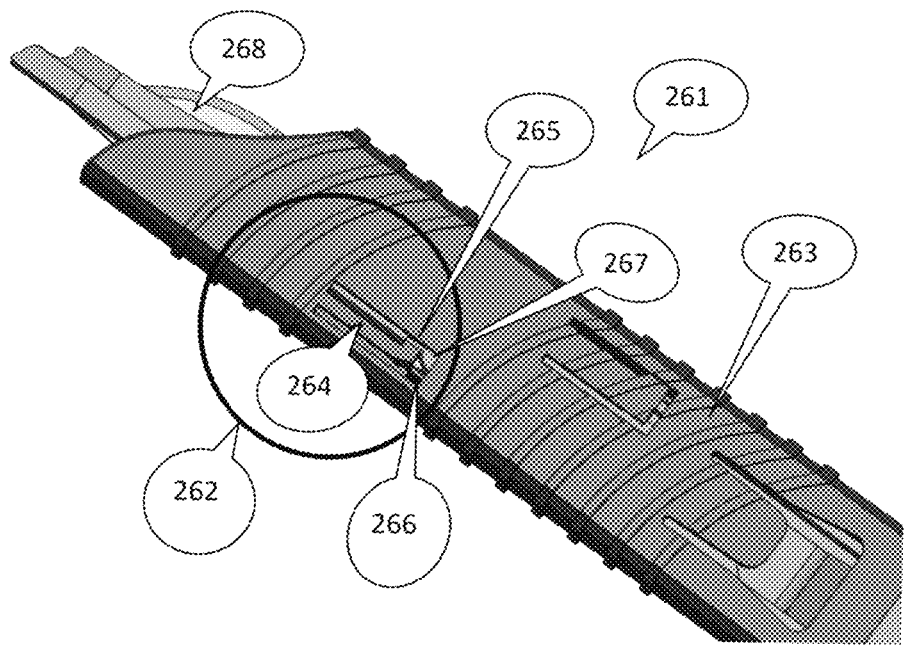
FIG. 26A and FIG. 26B are rear views of a safety scalpel having a handle and a blade cartridge releasably attached to the handle.
Figure 26B:
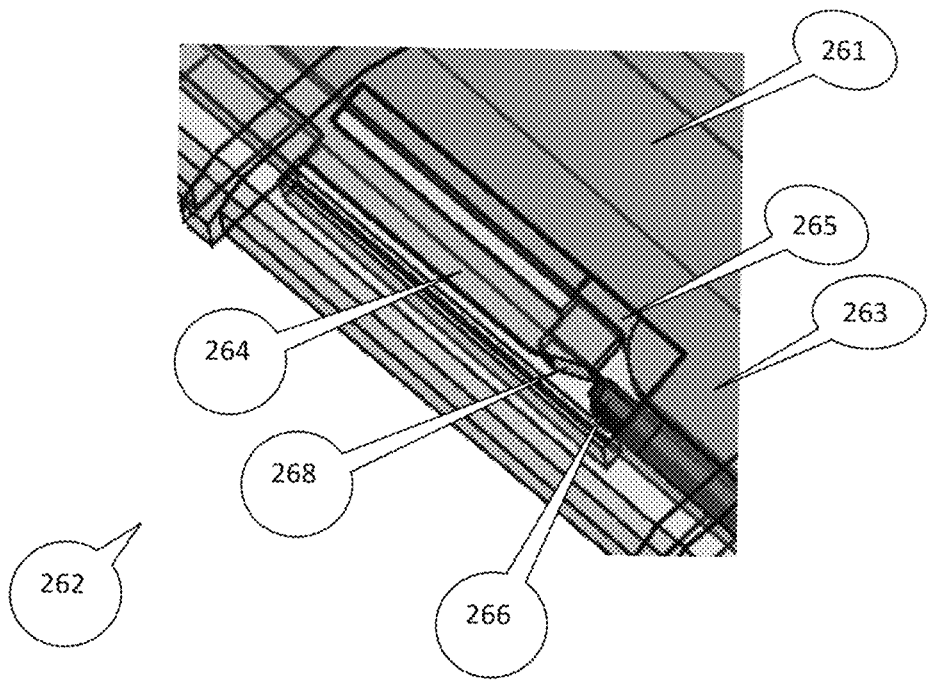

FIGS. 26A and 26B shows rear views of another example safety scalpel 261 having a blade holder 266 and a handle 267 that is similar to the example described with reference to FIGS. 2A and 2B with similar elements having the same name. A blade cartridge 263 is releasably attached to the handle 267. The resilient lock member 10 in FIGS. 2A and 2B is similar to the resilient lock member 264 in FIGS. 26A and 26B. The locking aperture 11 in FIGS. 2A and 2B is similar to the locking aperture 265 residing on a handle in FIGS. 26A and 26B. The only difference however is that the resilient lock member 264 comprises a sloped surface 268 (or inclined surface), which assists the blade holder 266 to push the resilient lock member 264 into the locking aperture 265 when the blade holder 266 is sliding into a cutting state wherein a blade 268 held by the blade holder 266 is in a cutting position.

Figure 27A:
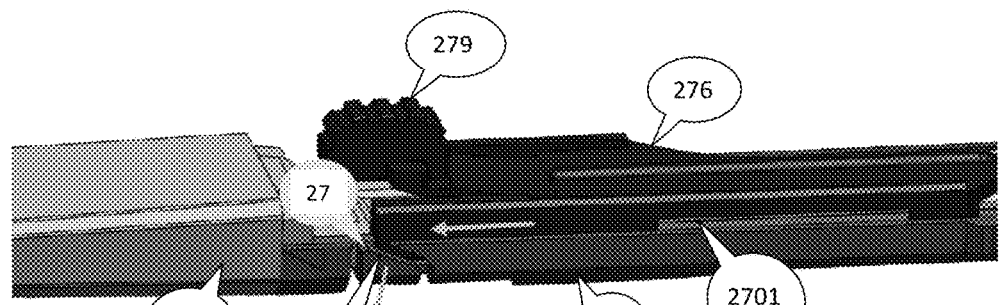
FIG. 27A is a partial perspective cross section view of a mid-section of a safety scalpel.
Figure 27B:
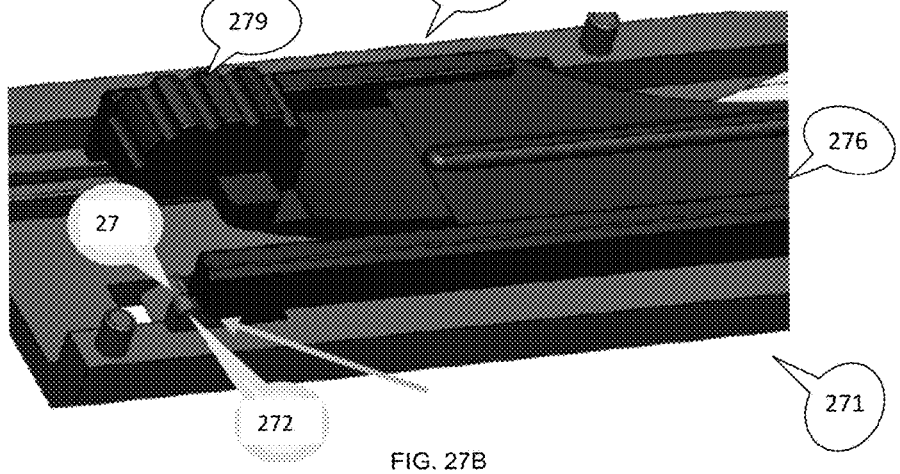
FIG. 27B is a partial perspective cross section view of the mid-section of the safety scalpel in FIG. 27A.
Figure 27C:
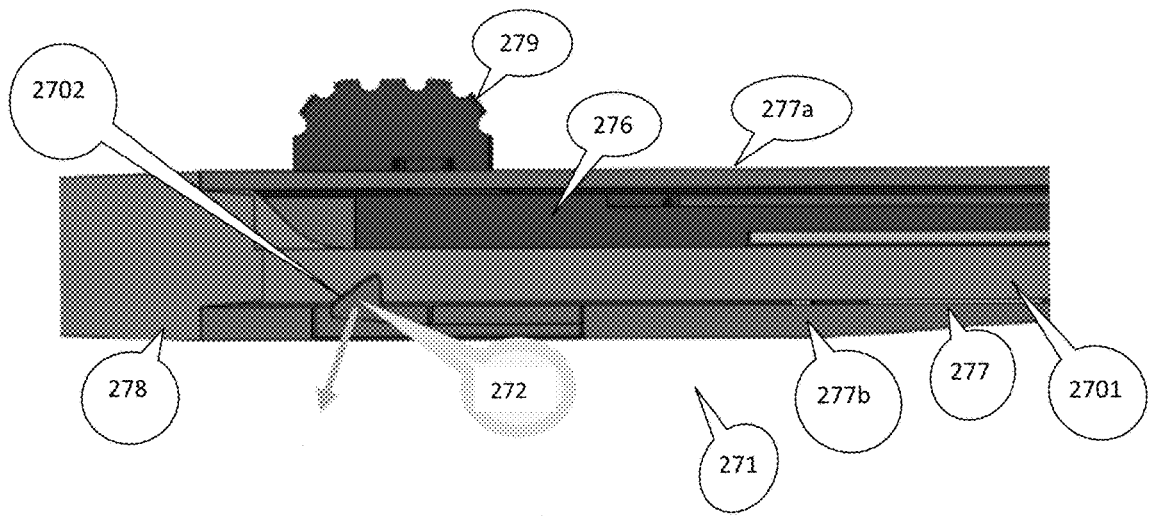
FIG. 27C is a cross section view of the safety scalpel illustrating a resilient lock member in FIG. 27A.

FIG. 27A, FIG. 27B and FIG. 27C illustrate partial cross section views (FIG. 27A and FIG. 27B) and cross section view (FIG. 27C) of a mid-section of another example safety scalpel 271 having a handle 278. A blade cartridge 277 (partially shown in FIGS. 27A, 27B and 27C) located on an outermost surface of the safety scalpel 271 is releasably attached to an extension 2701 of the handle 278. Parts 277*a* and 277*b* in FIG. 27C denote top and bottom sides of the blade cartridge 277. A blade holder 276 holding a blade (not shown in FIG. 27A) is disposed between the blade cartridge 277 and the handle 278. In FIG. 27B, the handle 278 is removed in the drawing to provide better visibility of the features of the blade cartridge 277 and the blade holder 276.

The blade holder 276 has a push assistant 279 (or an activation member) having a corrugated surface to assist a user to push and slide the blade holder 276 against the extension 2701 of the handle 278. The corrugated surface provides friction to aid the pushing. Most of the blade holder 276 except for the push assistant 279 resides in the blade cartridge 277. The blade holder 276 is configured to allow the blade (not shown in FIGS. 27A, 27B and 27C) to extend between a stowed position in a pre-cutting state of the blade holder 276 and a cutting position upon activation of the blade holder 276. The blade holder 276 is in the pre-cutting state when the blade (not shown in FIGS. 27A, 27B and 27C) is in the stowed position. The blade holder 276 is configured to slide along the extension 2701 of the handle 278. The extension 2701 of the handle 278 acts as a support for holding the blade holder 276. The blade cartridge 277 to inserted into the extension 2701.

A releasable scalpel snap 272 (or resilient lock member) is disposed within a housing of the blade cartridge 277. The releasable scalpel snap 272 (or resilient lock member) is coupled to an adjacent inclined portion 27. The releasable scalpel snap 272 is configured to move in tandem and in a same direction as the inclined portion 27 when the inclined portion 27 is moved. Both the snap 272 and the inclined portion 27 are shaped to protrude in a direction towards the extension 2701 of the handle 278. The extension 2701 of the handle 278 has a recessed portion 2702 for housing the protrusion of the snap 272. However, the shape of the snap 272 protrudes more in the direction towards the extension 2701 of the handle 278 compared to the protrusion of the inclined portion 27. It is appreciated that the snap 272 can be separately mounted to the housing of the blade cartridge 277 instead of being integral in another example.

The snap 272 is adapted to lock to the handle 278 in a default configuration (or unbiased condition) where the blade holder 276 is extended to set the blade (not shown in FIGS. 27A, 27B and 27C) in the cutting position. The snap 272 is adapted to disengage from the handle 278 when the blade holder 276 is retracted to set the blade (not shown in FIGS. 27A, 27B and 27C) in the stowed position. The adjacent inclined portion 27 comprises a slope 273 inclined in a manner such that when the blade holder 276 is moved to retract fully, the blade holder 276 will slide to abut against or engage the slope 273 of the inclined portion 27. The portion of the blade holder 276 abutting against the slope 273 can be deemed as an activation member. As the inclined portion 27 is abut against or pushed by the blade holder 276 to move, the snap 272 moves in tandem with the pushed inclined portion 27 until the protrusion of the snap 272 disengages from the recessed portion 2702 of the extension 2701 of the handle 278. After blade retraction that is when the blade holder 276 is retracted fully, removal of the blade cartridge 277 together with the blade holder 276 residing in the blade cartridge 277 from the handle 278 is allowed as the snap 272 would have disengaged (or unlocked) from the recessed portion 2702 of the extension 2701. During blade extension to the cutting position, the blade holder 276 slides away from the snap 272 and no longer abuts the inclined portion 27. This causes the snap 272 to revert back to lock to the extension 2701 of the handle 278 by having the protrusion of the snap 272 sit in the recessed portion 2702 of the extension 2701. When the protrusion of the snap 272 is in the recessed portion 2702, the blade cartridge 277 along with the blade holder 276 are fitted to the handle 278 and not allowed to be removed from the handle 278.

In addition, in all the above embodiments, the handle, and in particular, the surfaces for gripping such as the holding portion of the handle, may be made of or coated with a anti-slip material such as rubber material that can improve the friction between the hand and the grip surfaces. For example, the holding portion may be coated with a synthetic rubber material. The handle can be made of a metal material suitable for surgical applications. The blade housing, the blade holder, and the activation member can be made of materials not limited to plastics, such as a thermoplastic material such as for example, polycarbonate materials, plastics with resilient material properties. Still further, the blade housing, the blade holder, and the activation member may be injection molded or manufactured by 3D printing. Whilst there has been described in the foregoing description embodiments of the invention, it will be understood by those skilled in the technology concerned that many variations or modifications in details of design or construction may be made without departing from the scope of the invention.

The invention claimed is:

1. A safety scalpel comprising:
a handle comprising a locking aperture;

a resilient lock member; and
a blade cartridge releasably attached to the handle, the blade cartridge comprising:
   a blade;
   a housing; and
   a blade holder in communication with the blade;
wherein the blade holder is configured to allow the blade to extend between a stowed position in a pre-cutting state of the blade holder and a cutting position upon activation of the blade holder;
wherein the resilient lock member is disposed within the housing;
wherein in the pre-cutting state of the blade holder, the resilient lock member is in an unbiased condition where the resilient lock member is disengaged from the locking aperture of the handle; and
wherein upon activation of the blade holder, the resilient lock member engages the blade holder and is moved by the blade holder into the locking aperture of the handle to lock the blade cartridge to the handle when the blade is in the cutting position.

2. The safety scalpel according to claim 1, wherein the resilient lock member is integral with the housing.

3. The safety scalpel according to claim 1, wherein the resilient lock member comprises a resilient arm portion and a catch extending from the resilient arm portion; and
   wherein the blade holder has a surface adapted to engage the resilient arm portion of the resilient lock member and allow the catch of the resilient lock member to be moved into the locking aperture of the handle to lock the blade cartridge to the handle when the blade is in the cutting position upon activation of the blade holder.

4. The safety scalpel according to claim 1, wherein the blade cartridge further comprises a blade lock mechanism having a ramp adapted to abut the blade holder to prevent movement of the blade in the stowed position before the handle is inserted.

5. The safety scalpel according to claim 1, wherein the blade cartridge further comprises a blade lock mechanism having a housing ramp provided on the housing, wherein a handle ramp is provided on the handle, wherein the handle ramp is adapted to push on a housing ramp upon insertion of the handle, to move the housing ramp out of an aperture in the blade holder.

6. The safety scalpel according to claim 1, wherein the blade holder includes an activation member configured to be pressed down to enable the blade to slide between the stowed position when the blade holder is in a pre-cutting state and the cutting position upon activation of the blade holder.

7. The safety scalpel according to claim 6, wherein the activation member is configured to engage the housing to prevent movement of the blade when the blade holder is in the pre-cutting state.

8. The safety scalpel according to claim 6 further comprising a flip guard provided above the activation member.

9. The safety scalpel according to claim 6, wherein the activation member includes an embedded button.

10. The safety scalpel according to claim 6 further comprising a slide guard provided below the activation member.

11. The safety scalpel according to claim 6 further comprising a button guard provided on the housing and around the activation member to prevent inadvertent activation of the blade holder.

12. The safety scalpel according to claim 3 further comprising a cartridge release mechanism arranged for allowing release of the blade cartridge upon exerting a force perpendicular to a direction of movement of the blade holder along a longitudinal axis of the handle.

13. The safety scalpel according to claim 12, wherein the cartridge release mechanism comprises a resilient lift tab provided on the blade cartridge; and
   wherein the lift tab is arranged adjacent a recess on the handle for allowing release of the blade cartridge when the blade is in the stowed position.

14. The safety scalpel according to claim 1, wherein the housing comprises a first housing part and a second housing part ultrasonically welded together to form the housing.

15. The safety scalpel according to claim 1, wherein the housing comprises a cantilever member adapted for releasably mounting the blade cartridge to the handle.

16. The safety scalpel according to claim 1, wherein the blade cartridge further comprises snap features located on opposing sides of the housing, wherein the snap features are adapted to releasably attach the blade cartridge to the handle.

17. The safety scalpel according to claim 1, wherein the blade cartridge further comprises a snap feature adapted to engage with an aperture in the handle.

18. The safety scalpel according to claim 1, wherein the blade cartridge further comprises a portion configured to move in tandem with the snap feature, and the portion is moveable by the blade holder.

19. A replaceable blade cartridge for releasably attaching to a handle to form a safety scalpel, the replaceable blade cartridge comprising
   a blade;
   a housing;
   a blade holder in communication with the blade, wherein the blade holder is configured to allow the blade to extend between a stowed position in a pre-cutting state of the blade holder and a cutting position upon activation of the blade holder; and
   a resilient lock member disposed within the housing, wherein the resilient lock member is in an unbiased condition when the blade holder is in the pre-cutting state such that the resilient lock member is configured to disengage a locking aperture of the handle, and wherein the resilient lock member is configured to engage the blade holder to lock the blade cartridge to the handle only when the blade is in the cutting position upon activation of the blade holder;
   wherein the resilient lock member comprises a resilient arm portion and a catch extending from the resilient arm portion; and
   wherein the blade holder has a surface adapted to engage the resilient arm portion of the resilient lock member and allow the catch of the resilient lock member to be moved into the locking aperture of the handle to lock the blade cartridge to the handle when the blade is in the cutting position upon activation of the blade holder.

20. The replaceable blade cartridge according to claim 19, wherein the resilient lock member is integral with the housing.

21. The replaceable blade cartridge according to claim 19, wherein the blade holder includes an integral activation member configured to be pressed down to enable sliding of the blade holder and the blade.

22. The replaceable blade cartridge according to claim 19, wherein the activation member is configured to engage the housing to prevent movement of the blade when the blade holder is in the pre-cutting state.

23. The replaceable blade cartridge according to claim 19, wherein the activation member includes an embedded button.

24. A safety scalpel comprising:
a handle comprising a locking aperture;
a resilient lock member comprising a resilient arm portion and a catch extending from the resilient arm portion; and
a blade cartridge releasably attached to the handle comprising:
  a blade;
  a housing having disposed therein the resilient lock member; and
  a blade holder in communication with the blade comprising a surface;
wherein the blade holder has a pre-cutting state in which the blade is in a stowed position where the resilient lock member is in an unbiased condition and the resilient lock member is disengaged from the locking aperture of the handle;
wherein upon activation of the blade holder, the surface of the blade holder engages the resilient arm portion of the resilient lock member and allows the catch of the resilient lock member to move into the locking aperture of the handle to lock the blade cartridge to the handle when the blade is in the cutting position; and
wherein the blade holder is configured to allow the blade to move between and into the stowed position and the cutting position and vice versa.

* * * * *